US012599363B2

(12) United States Patent
Lee et al.

(10) Patent No.: US 12,599,363 B2
(45) Date of Patent: Apr. 14, 2026

(54) WEARABLE DEVICE FOR HANDS-FREE OPERATION OF AN ULTRASOUND PROBE

(71) Applicant: GE Precision Healthcare LLC, Waukesha, WI (US)

(72) Inventors: Warren Lee, Niskayuna, NY (US); David Shoudy, Niskayuna, NY (US); Andrew Burns, Niskayuna, NY (US); Craig Galligan, Averill Park, NY (US)

(73) Assignee: GE Precision Healthcare LLC, Waukesha, WI (US)

( * ) Notice: Subject to any disclaimer, the term of this patent is extended or adjusted under 35 U.S.C. 154(b) by 8 days.

(21) Appl. No.: 18/645,015

(22) Filed: Apr. 24, 2024

(65) Prior Publication Data

US 2025/0331814 A1 Oct. 30, 2025

(51) Int. Cl.
*A61B 8/00* (2006.01)

(52) U.S. Cl.
CPC .......... *A61B 8/4227* (2013.01); *A61B 8/4245* (2013.01); *A61B 8/4455* (2013.01)

(58) Field of Classification Search
CPC .... A61B 8/4227; A61B 8/4245; A61B 8/4455
See application file for complete search history.

(56) References Cited

U.S. PATENT DOCUMENTS

| | | | |
|---|---|---|---|
| 5,381,794 A | 1/1995 | Tei et al. | |
| 6,048,323 A | 4/2000 | Hon | |
| 6,261,231 B1 | 7/2001 | Damphousse et al. | |
| 11,272,902 B2 | 3/2022 | Geelen et al. | |
| 2016/0302766 A1 | 10/2016 | Liu et al. | |
| 2018/0263597 A1* | 9/2018 | Tchang .................. | A61B 90/50 |

FOREIGN PATENT DOCUMENTS

| | | | | |
|---|---|---|---|---|
| AU | 2019216618 A1 * | 9/2019 | ............ | A61B 34/10 |
| CA | 3229348 A1 * | 2/2023 | ............ | A61B 8/565 |
| CN | 101856243 B | 5/2013 | | |
| CN | 109223040 A | 1/2019 | | |
| CN | 220544610 U * | 2/2024 | | |

OTHER PUBLICATIONS

CN-220544610 machine translation (Year: 2024).*

* cited by examiner

*Primary Examiner* — Alexei Bykhovski
(74) *Attorney, Agent, or Firm* — SPQ IP LLC

(57) ABSTRACT

A wearable device is provided. The wearable device may include a mount including a spherical outer surface, and an opening configured to receive a probe. The wearable device may include a base comprising an inner circumferential surface that interfaces with the spherical outer surface of the mount to selectively rotate the mount about at least one axis of the base. The wearable device may include a lock that locks a position of the probe relative to the mount and that locks the probe at an orientation relative to the base.

20 Claims, 29 Drawing Sheets

100

150

152          153          151

117          116

301

302

100

110

500

110

303

110

110

500

100

206

100

150

130

WEARABLE DEVICE FOR HANDS-FREE OPERATION OF AN ULTRASOUND PROBE

TECHNICAL FIELD

The present disclosure relates, generally, to a wearable device for hands-free operation of an ultrasound probe.

BACKGROUND

Ultrasound has various diagnostic and therapeutic applications. For example, ultrasound may be used for imaging regions of interest, measuring physiological characteristics, heating or ablating tissue, or the like. In most cases, the positioning and orienting of the ultrasound probe relative to the region of interest and the skin surface of a subject have a significant effect on the quality of such applications. In some cases, such as cardiac monitoring applications, operation of the ultrasound probe might be intended for a relatively long duration. In these cases, it might be infeasible or error-prone for a subject or a sonographer to hold the ultrasound probe at a particular position and/or orientation for the entire duration of the operation of the ultrasound probe. Further, some wearable devices might be difficult to install on a subject, might have non-intuitive adjustment, might not permit secure locking, might not be ergonomic or comfortable, might not accommodate a wide variety of body shapes, or the like. Accordingly, in these cases, the quality or accuracy of the ultrasound imaging, monitoring or therapy might be significantly reduced, and the user experience might be reduced.

SUMMARY

This summary introduces concepts that are described in more detail in the detailed description. It should not be used to identify essential features of the claimed subject matter, nor to limit the scope of the claimed subject matter.

According to an aspect, a wearable device may include a mount including a spherical outer surface, and an opening configured to receive a probe. The wearable device may include a base comprising an inner circumferential surface that interfaces with the spherical outer surface of the mount to selectively rotate the mount about at least one axis of the base. The wearable device may include a lock that locks a position of the probe relative to the mount and that locks the probe at an orientation relative to the base.

According to an aspect, the mount may include a first channel, the base may include a second channel, and the lock may close, or narrow, the first channel and the second channel to lock the position of the probe relative to the mount and lock the probe at the orientation relative to the base.

According to an aspect, the wearable device may include one or more strap connectors that attach a strap to the base and that are lockable at different angular positions.

According to an aspect, the lock may lock an amount of protrusion of the probe below a contact surface of the base.

According to an aspect, the wearable device may include an adapter that attaches to the probe, and that interfaces with an internal surface of the opening of the spherical mount.

According to an aspect, the wearable device may include a cup that attaches to the base and that contacts a surface of a wearer of the wearable device.

According to an aspect, the cup may be conformable to the surface of the wearer of the wearable device.

According to an aspect, the cup may include a substantially circular profile.

According to an aspect, the cup may include a substantially elliptical profile.

According to an aspect, the probe may include one or more stops that prevent movement of the probe beyond a particular position with respect to the mount.

According to an aspect, the base may include an integrated cable hook that secures a cable of the probe.

According to an aspect, the base may include a first keyed feature that interfaces with a second keyed feature of a cup to lock an orientation of the cup relative to the base.

According to an aspect, the wearable device may include one or more strap connectors that are lockable at positions located above a contact surface of the base.

According to an aspect, the probe may include a section having a substantially non-uniform profile. The wearable device may include an adapter that includes an inner surface that attaches to the section of the ultrasound probe, and that includes an outer surface that interfaces with an inner surface of the mount to permit the probe to move relative to the mount.

According to an aspect, the base may include rotational fiducial markings, the mount may include a rotational fiducial indicator, or the probe may include fiducial markings.

According to an aspect, the probe may include a ball, the mount may include a detent, and the ball may engage with the detent to hold the wearable device off of a surface of a wearer of the wearable device.

According to an aspect, the wearable device may include one or more straps to secure the wearable device to a wearer of the wearable device, and a set of strap connectors corresponding to the one or more straps to connect the one or more straps to the base.

According to an aspect, the probe may include a section having a substantially uniform profile to permit the probe to move relative to the mount.

According to an aspect, the probe may be an ultrasound probe.

According to an aspect, the lock may be the only lock of the wearable device that locks the position of the probe relative to the mount and that locks the probe at the orientation relative to the base.

DETAILED DESCRIPTION

As addressed above, some ultrasound applications may involve extended durations of ultrasound imaging or monitoring, and may require precise positioning of the ultrasound probe with respect to a subject. Some embodiments of the present disclosure provide a wearable device that, among other things, is easy to install on a subject, provides rapid and intuitive positioning and adjustment of the ultrasound probe relative to the subject, provides easy and secure locking of the position and orientation of the ultrasound probe, is ergonomic and comfortable for the subject, provides flexible adjustment to accommodate a wide variety of body shapes, and provides improved contact between the ultrasound probe and the subject. In this way, some embodiments of the present disclosure improve the viability and efficacy of hands-free ultrasound imaging or monitoring for a wide variety of ultrasound applications.

Figure 1:
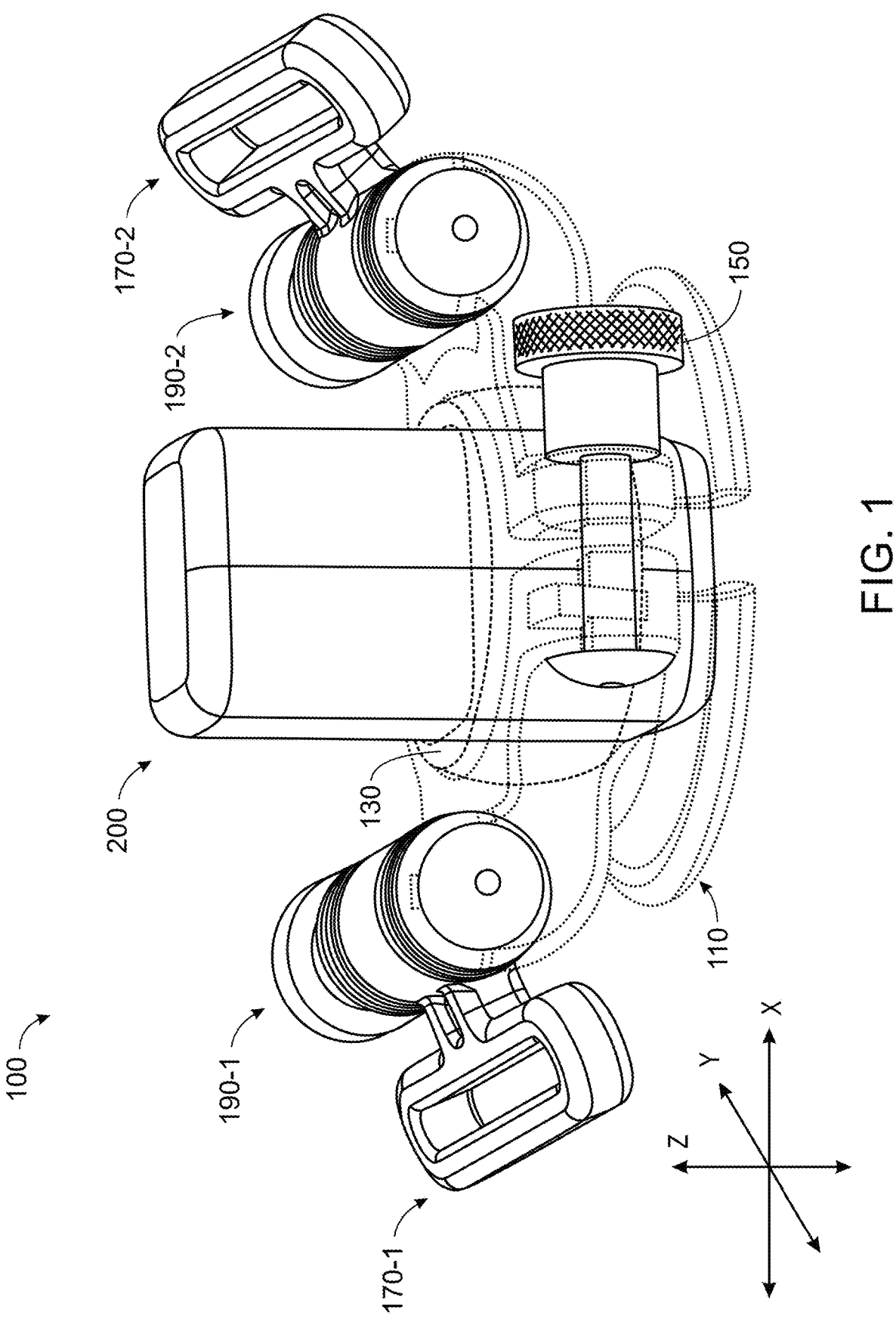
FIG. 1 is a diagram of a wearable device for hands-free operation of an ultrasound probe.
Figure 2:
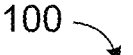
FIG. 2 is a diagram of the wearable device attached to a subject.

FIG. 1 is a diagram of a wearable device 100 for hands-free operation of an ultrasound probe 200. As shown in FIG. 1, the wearable device 100 may include a base 110, a mount 130, a lock 150, a first strap connector 170-1, a second strap connector 170-2, a first strap connector lock 190-1, and a second strap connector lock 190-2. The base 110 provides support for the mount 130, the lock 150, the first strap connector 170-1, the second strap connector 170-2, the first strap connector lock 190-1, and the second strap connector lock 190-2. According to an embodiment, the base 110 may be configured to rest on a surface of a subject, and allow positioning and orienting of the ultrasound probe 200 with respect to the subject. The base 110 may be comprised of any suitable material such as a polymer, a composite, a ceramic, a metal, or the like. The mount 130 attaches to the ultrasound probe 200, and interfaces with the base 110 to rotate the ultrasound probe 200 about multiple axes (e.g., the x-axis, the y-axis, and the z-axis shown in FIG. 1) of the base 110. The mount 130 may be comprised of any suitable material such as a polymer, a composite, a ceramic, a metal, or the like. The lock 150 may lock a position of the ultrasound probe 200 relative to the mount 130 and lock the ultrasound probe 200 at an orientation relative to the base 110. The lock 150 may include a bolt mechanism, a cam mechanism, a lever mechanism, or the like. The first strap connector 170-1 and the second strap connector 170-2 may provide connection points for a strap 300 (as shown in FIG. 2), and may be lockable at different angular positions via the first strap connector lock 190-1 and the second strap connector lock 190-2. The first strap connector 170-1 and the second strap connector 170-2 may be rotatable about a single axis or multiple axes, and may be lockable at different positions about the single axis or the multiple axes. For example, the first strap connector 170-1 and the second strap connector 170-2 may be rotatable through an angular range (e.g., ±5°, ±10°, ±15°, ±20°, ±30°, ±45°, etc.) about one or more axes. In this way, the first strap connector lock 190-1 and the second strap connector lock 190-2 may lock the first strap connector 170-1 and the second strap connector 170-2 at various angular positions through the angular range. Further, in this way, the first strap connector 170-1 and the second strap connector 170-2 may be lockable at positions located above the plane of the mount 130 and above the contact surface of the base 110, which permits an increase in downforce applied to the surface of the subject by the ultrasound probe 200. The first strap connector 170-1 and the second strap connector 170-2 may be comprised of any suitable material such as a polymer, a composite, a ceramic, a metal, or the like. The first strap connector lock 190-1 and the second strap connector lock 190-2 may respectively lock the first strap connector 170-1 and the second strap connector 170-2 at the same or different angular positions relative to each other. The first strap connector lock 190-1 and the second strap connector lock 190-2 may include a Hirth mechanism, a bolt mechanism, a cam mechanism, a lever mechanism, a ball joint mechanism, or the like.

The ultrasound probe 200 may be a linear probe, a phased array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a probe having a single element transducer, a probe having a transducer array, or the like. According to an embodiment, the ultrasound probe 200 may be configured to generate ultrasound signals, emit the ultrasound signals towards a region of interest of a subject, receive echo ultrasound signals that are back-scattered from the region of interest of the subject, generate ultrasound data based on the echo ultrasound signals, and output the ultrasound data for diagnostic applications, such as ultrasound imaging or ultrasound monitoring. According to another embodiment, the ultrasound probe 200 may be configured to generate ultrasound signals, and emit the ultrasound signals towards a region of interest of a subject for therapeutic applications, such as tissue ablation, tissue warming, tissue tightening, ultrasound-based neuromodulation, or the like. According to another embodiment, the ultrasound probe 200 may be configured for diagnostic applications and therapeutic applications. For example, the ultrasound probe 200 may include one or more transducers configured for diagnostic applications, and may include one or more transducers configured for therapeutic applications. Although some embodiments include the ultrasound probe 200, it should be understood that the embodiments herein are applicable to other types of probes associated with different imaging modalities or thera- peutic modalities. For example, the embodiments herein are applicable to probes for photoacoustic imaging, or the like.

FIG. 2 is a diagram of the wearable device 100 attached to a subject. As shown in FIG. 2, the wearable device 100 may be attached to the subject via the strap 300 to permit hands-free ultrasound applications, such as diagnostic appli- cations, therapeutic applications, or the like. The subject, also referred to as a "wearer" of the wearable device 100, may be a human, an animal, a phantom, or the like. The wearable device 100 may be attached to any anatomical position of the subject and may permit ultrasound imaging of any region of interest of the subject, ultrasound monitor- ing of any physiological characteristic (e.g., cardiac output, heart rate, or the like) of the subject, ultrasound therapy of any region of interest of the subject, or the like.

Figure 3:
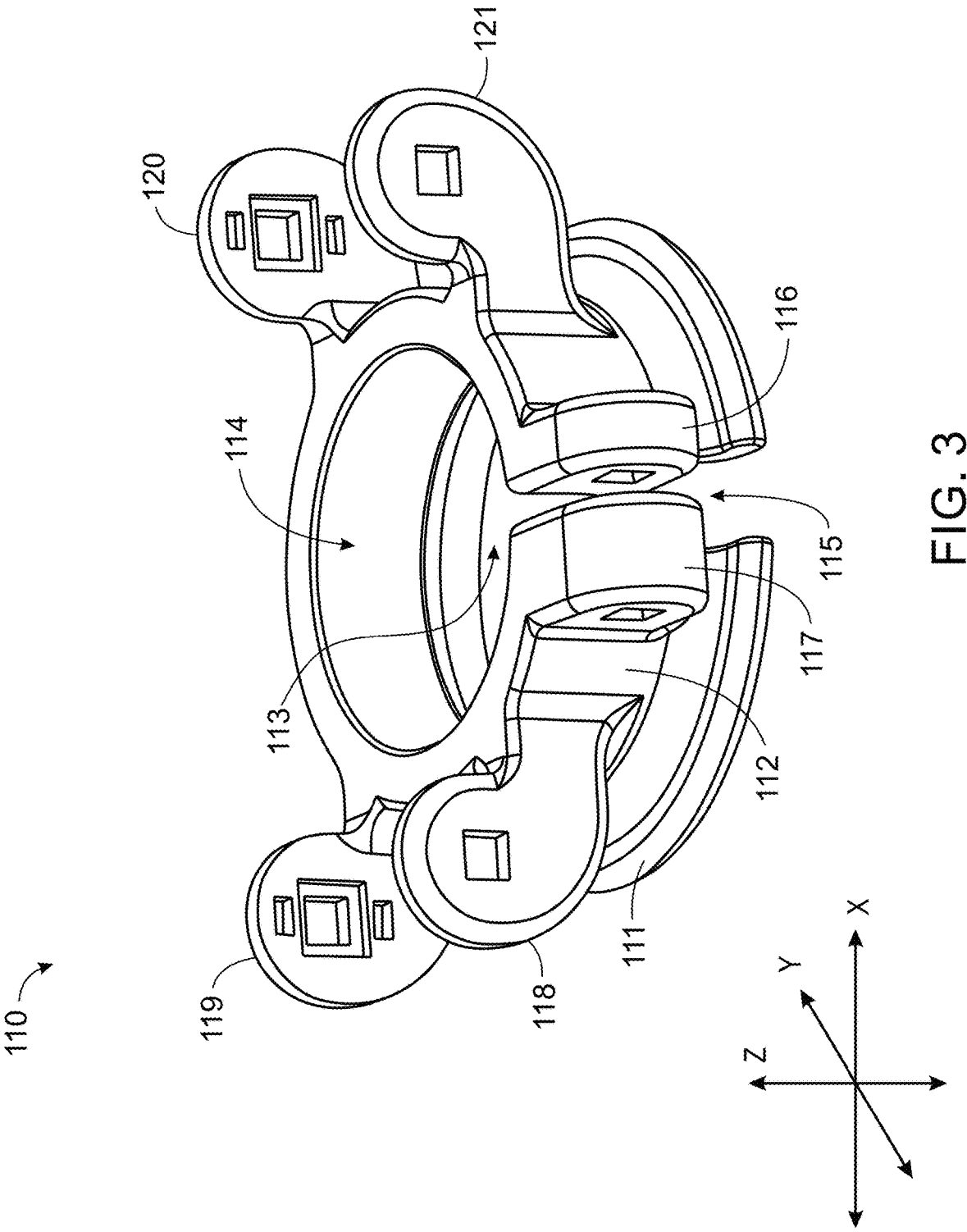
FIG. 3 is a diagram of the base of the wearable device.

FIG. 3 is a diagram of the base 110 of the wearable device 100. As shown in FIG. 3, the base 110 may include a bottom portion 111, a top portion 112, an opening 113, an inner circumferential surface 114, a channel 115, a first lock portion 116, a second lock portion 117, a first strap attach- ment portion 118, a second strap attachment portion 119, a first strap portion 120, and a second strap portion 121. The bottom portion 111 may be annular, and interface directly or indirectly with a surface of the subject. The top portion 112 may be annular and extend perpendicularly from the bottom portion 111. The top portion 112 may define the opening 113, and include the inner circumferential surface 114. The channel 115 may allow the base 110 to compress when the lock 150 is locked. For example, when locked, the lock 150 may close the channel 115 such that the increased friction between the mount 130 and the base 110 prevents motion of the mount 130. Alternatively, the lock 150, when locked, may narrow the channel 115 such that the increased friction between the mount 130 and the base 110 prevents motion of the mount 130. According to an embodiment, the size of the channel 115 between the first lock portion 116 and the second lock portion 117 may be substantially the same size. Alternatively, the size of the channel 115 between the first lock portion 116 and the second lock portion 117 may be smaller than the size of the channel 115 at the bottom portion 111. In this way, if the channel 115 is fully closed between the first lock portion 116 and the second lock portion 117, the channel 115 would still be open at the bottom portion 111, thereby preventing pinching of the subject. According to an embodiment, and as shown in FIG. 3, the channel 115 may be oriented substantially perpendicular to a bottom surface of the bottom portion 111. Alternatively, the channel 115 may be oriented parallel to the bottom surface of the bottom portion 111. Alternatively, the channel 115 may be oriented at an angle with respect to the bottom surface of the bottom portion 111 (e.g., 25°, 35°, 45°, 60°, 70°, or the like). The first lock portion 116 and the second lock portion 117 may provide support for the lock 150, and permit the lock 150 to be connected to the base 110. The first lock portion 116 and the second lock portion 117 may compress when the lock 150 is locked. The first strap attachment portion 118 and the second strap attachment portion 119 may provide support for the first strap connector 170-1, and permit the first strap connector 170-1 to be connected to the base 110 via the first strap connector lock 190-1. The first strap portion 120 and the second strap portion 121 may provide support for the second strap connector 170-2, and permit the second strap connector 170-2 to be connected to the base 110 via the second strap connector lock 190-2.

Figure 4:
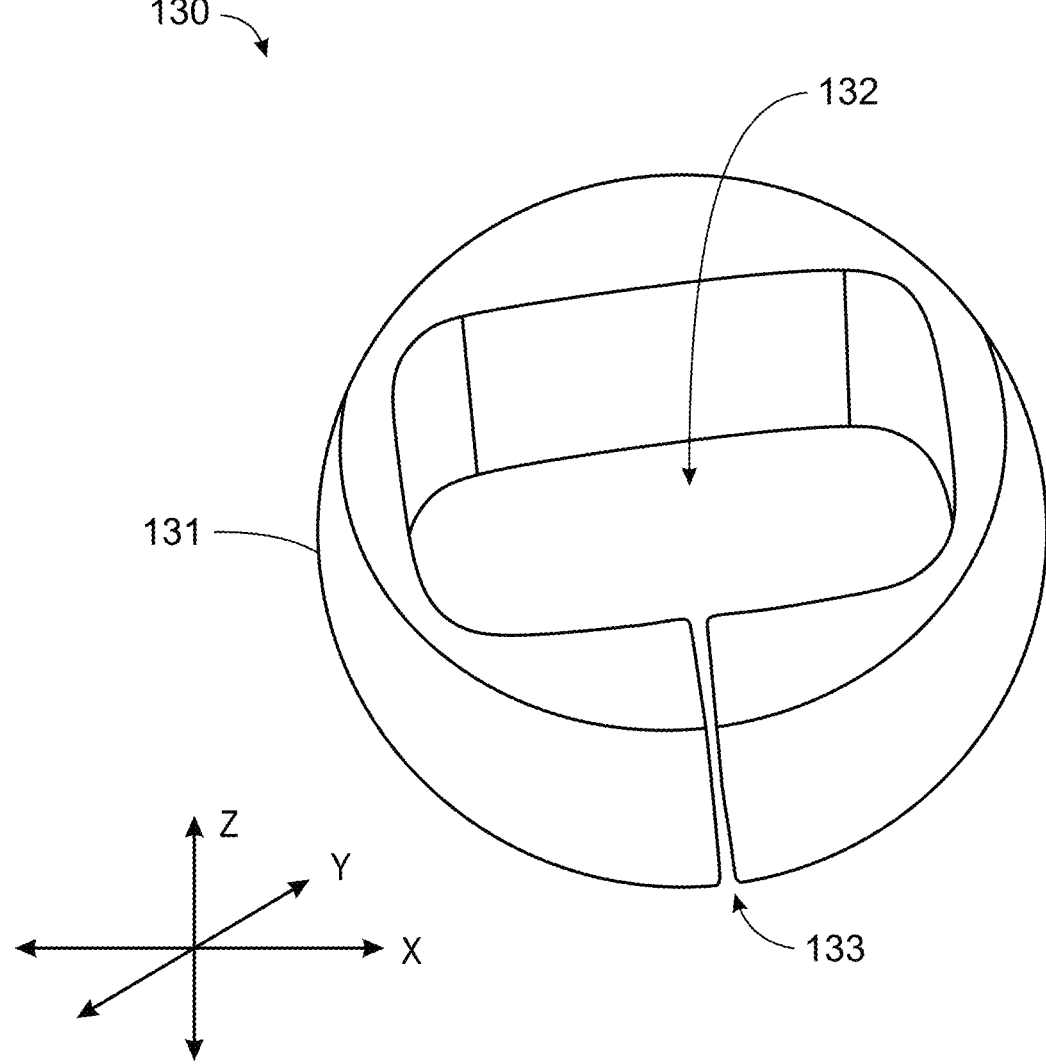
FIG. 4 is a diagram of the mount of the wearable device.

FIG. 4 is a diagram of the mount 130 of the wearable device 100. As shown in FIG. 4, the mount 130 may include a spherical outer surface 131, an opening 132, and a channel 133. The spherical outer surface 131 may interface with the inner circumferential surface 114 of the base 110 to selec- tively rotate the mount 130 about at least one axis of the base 110. The opening 132 may be configured to receive the ultrasound probe 200. The channel 133 may allow the mount 130 to compress to secure the probe 200 to the mount 130 when the lock 150 is locked. For example, when locked 150, the lock 150 may close the channel 133 such that the increased friction between the mount 130 and the ultrasound probe 200 prevents motion of the ultrasound probe 200. Alternatively, when locked, the lock 150 may narrow the channel 133 such that the increased friction between the mount 130 and the ultrasound probe 200 prevents motion of the ultrasound probe 200.

Figure 5:
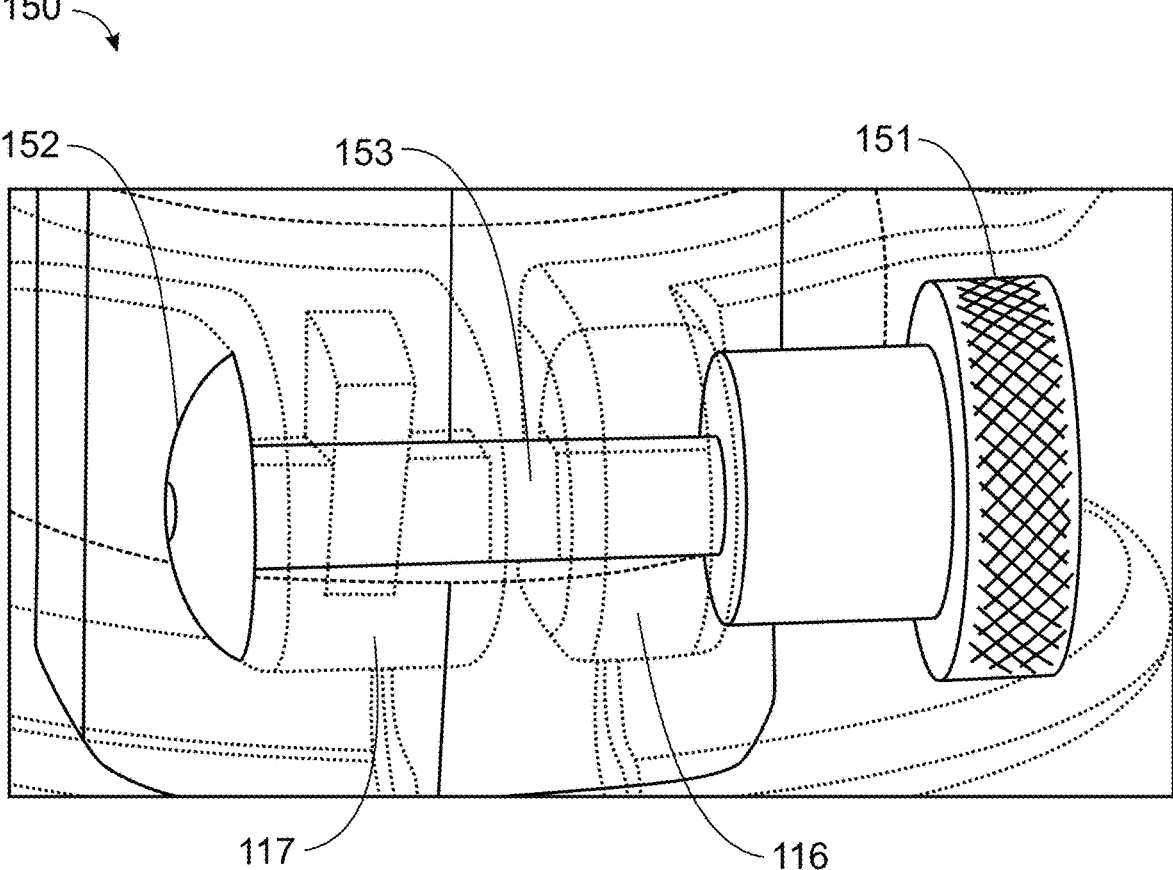
FIG. 5 is a diagram of the lock of the wearable device.

FIG. 5 is a diagram of the lock 150 of the wearable device 100. As shown in FIG. 5, the lock 150 may include a first portion 151, a second portion 152, and a third portion 153. The first portion 151 may define a first end of the lock 150, and permit the lock 150 to be manipulated by a user to lock the lock 150 and unlock the lock 150. The second portion 152 may define a second end of the lock 150, and anchor the lock 150 to the base 110. The third portion 153 may connect the first portion 151 and the second portion 152, and extend through the first lock portion 116 and the second lock portion 117 of the base 110.

Figure 6:
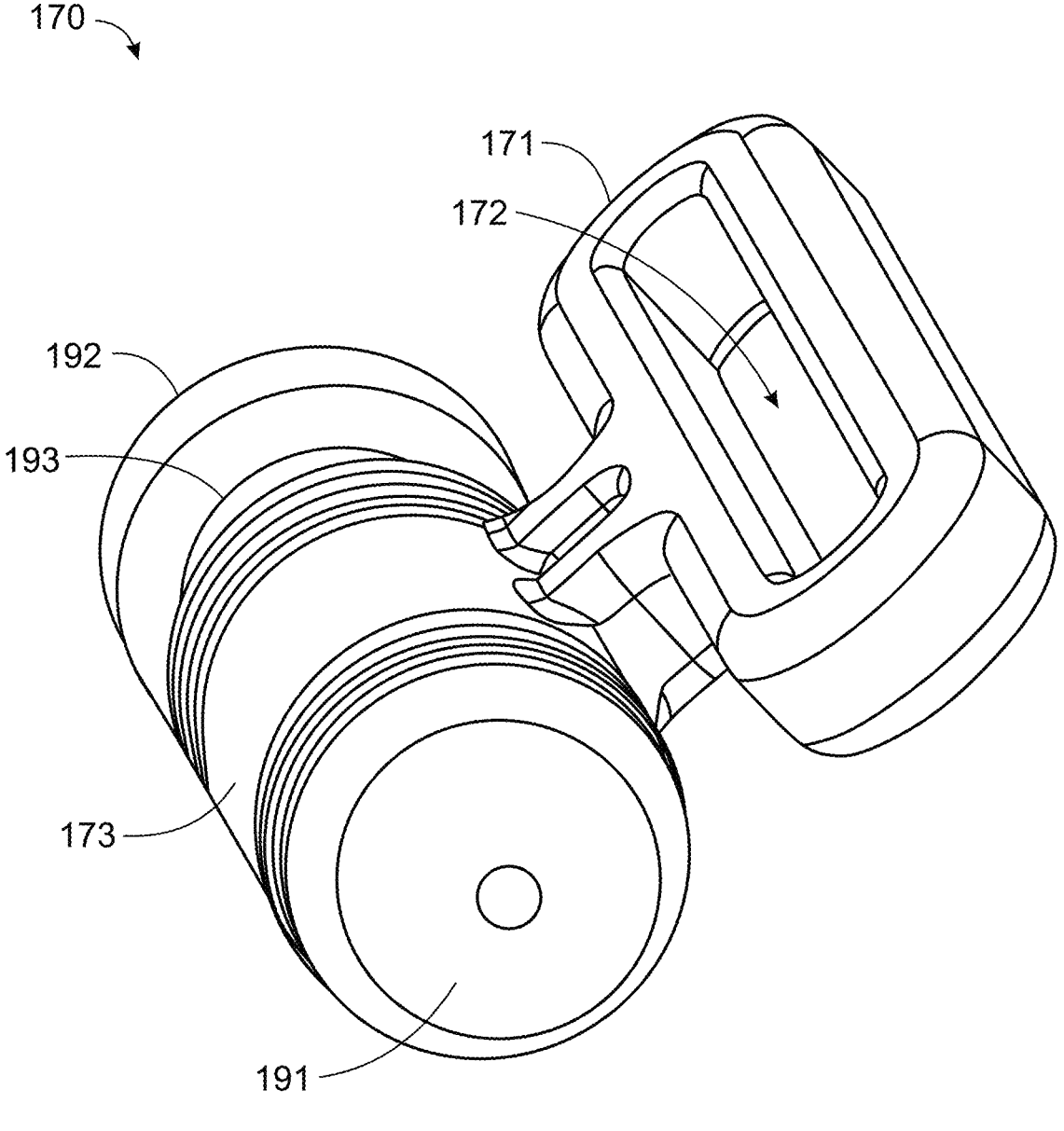
FIG. 6 is a diagram of a strap connector of the wearable device.

FIG. 6 is a diagram of a strap connector 170 of the wearable device 100. The strap connector 170 may include a first portion 171, an opening 172, and a third portion 173. The first portion 171 may define the opening 172, and permit connection of the strap 300 to the base 110. The opening 172 may permit the strap 300 to be connected to the strap connector 170. The third portion 173 may connect to the base 110 via the strap connector lock 190. The strap con- nector lock 190 may include a first portion 191 that defines a first end of the strap connector lock 190, a second portion 192 that defines a second end of the strap connector lock 190, and a third portion 193 that extends through the first strap portion 118 and the second strap attachment portion 119 or the first strap portion 120 and the second strap portion 121 of the base 110 to connect the strap connector 170 to the base 110.

Figure 7:
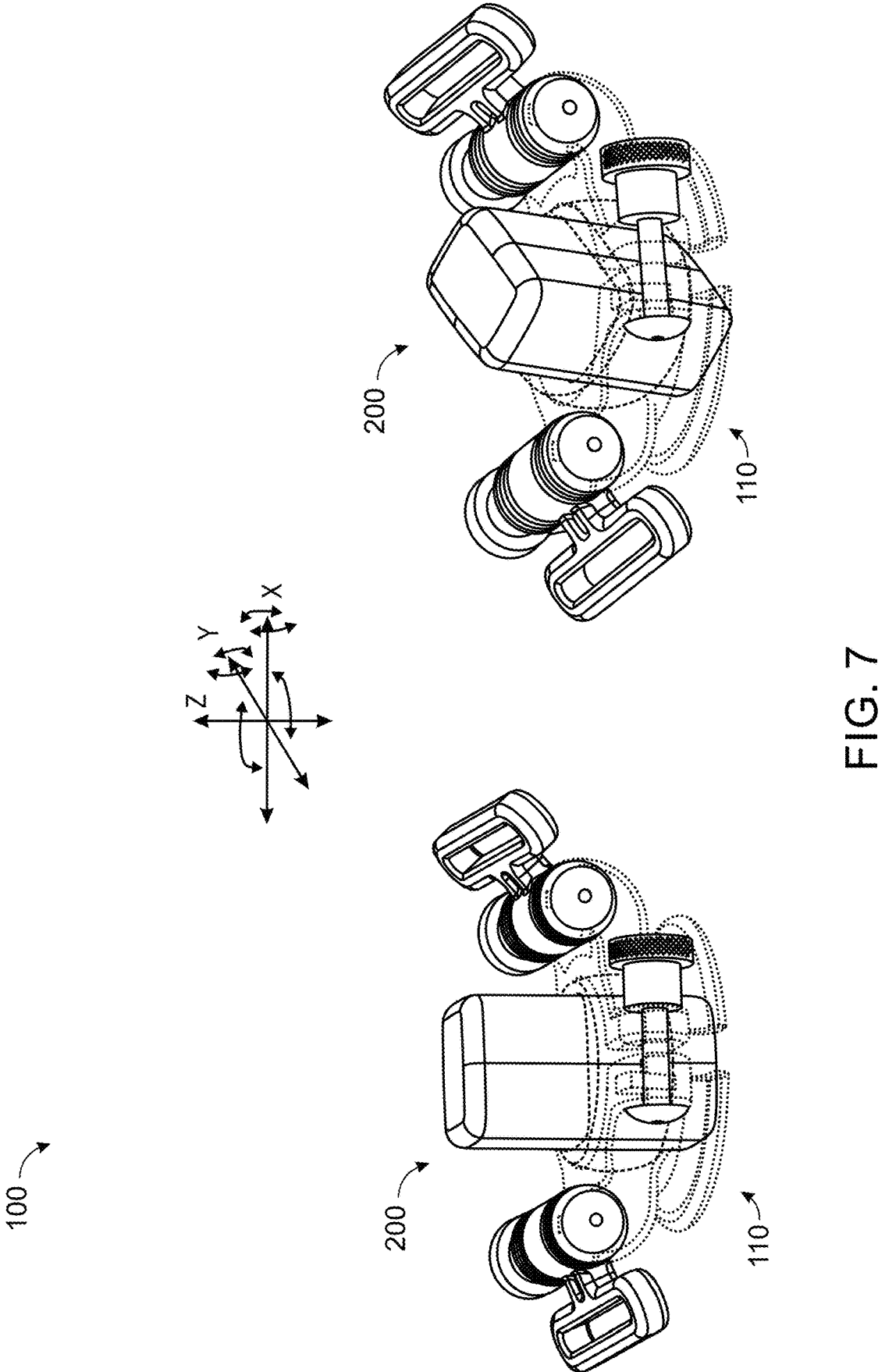
FIG. 7 is a diagram of orienting the ultrasound probe relative to the base.

FIG. 7 is a diagram of orienting the ultrasound probe 200 relative to the base 110. As shown in FIG. 7, the ultrasound probe 200 may be oriented at different orientations relative to the base 110. For example, as shown, the ultrasound probe 200 may be selectively rotated about multiple axes of the base 110 by interfacing the spherical outer surface 131 of the mount 130 with the inner circumferential surface 114 of the base 110. An operator may orient the ultrasound probe 200 at a desired orientation, and lock the orientation of the ultrasound probe 200 relative to the base 110 via the lock 150. In this way, the base 110 includes the inner circumfer- ential surface 114 that interfaces with the spherical outer surface 131 of the mount 130 to form a ball joint, which enables rotation about all three axes and, therefore, arbitrary angulation of the ultrasound probe 200 with respect to the base 110. The base 110 and mount 130 may be configured with small clearances to enable low friction movement when the lock 150 is unlocked. In addition, the opening 132 of the mount 130 may have a small clearance to the ultrasound probe 200 to permit low friction movement when the lock 150 is unlocked. After the desired position of the ultrasound probe 200 relative to the mount 130 and the desired orientation of the ultrasound probe 200 relative to the base 110 are found, the operator may lock the lock 150 which compresses the first lock portion 116 and the second lock portion 117 toward each other. The action forces a reduction in the channel 115 between the first lock portion 116 and the second lock portion 117 such that the base 110 contacts the mount 130, which in turn compresses the channel 133 in the mount 130, thereby causing the mount 130 to clamp the ultrasound probe 200. Therefore, the position of the ultrasound probe 200 with respect to the mount 130 and the orientation of the ultrasound probe 200 with respect to the base 110 are reversibly locked through an increase in friction between the outer surface of the ultrasound probe 200 and the interior surface of the opening 132 of the mount 130 and between the spherical outer surface 131 of the mount 130 and the inner circumferential surface 114 of the base 110.

The ultrasound probe 200 may be arbitrarily oriented with respect to the base 110 when manipulated by the operator. For example, the ultrasound probe 200 may be rotated about the X-axis, Y-axis, and Z-axis as shown in FIG. 7. In this case, "tilt" may refer to rotation about the X-axis shown in FIG. 7, "rock" may refer to rotation about the Y-axis as shown in FIG. 7, and "spin" may refer to rotation about the Z-axis as shown in FIG. 7. The achievable range of angles in rock, tilt, and/or spin may vary based on the configured size of the base 110, the mount 130, and the ultrasound probe 200. Further, the achievable range of angles of rock, tilt, and/or spin may be limited by, or dependent on, an orientation of the ultrasound probe 200. In other words, and as an example, an amount of rock may be limited by, or dependent on, an amount of tilt or spin of the ultrasound probe 200. According to an embodiment, the wearable device 100 may be configured to permit a particular amount of rock (e.g., ±5°, ±10°, ±15°, ±20°, ±30°, ±45°, etc.), a particular amount of tilt (e.g., ±5°, ±10°, ±15°, ±20°, ±30°, ±45°, etc.), and a particular amount of spin (e.g., ±180°, ±270°, ±360°, etc.) of the ultrasound probe 200 in reference to an initial orientation of the ultrasound probe 200. It should be understood that the amount of achievable angles of tilt, rock, and spin may depend on the geometries and characteristics of the base 110, the mount 130, and the ultrasound probe 200.

According to an embodiment, the base 110 is configured to initially orient the ultrasound probe 200 at a particular angle. For example, the ultrasound probe 200 may be initially oriented with a preconfigured amount of tilt, rock, and/or spin when the wearable device 100 is placed on the subject. As a particular example, the ultrasound probe 200 may be initially oriented with substantially 0° of tilt, rock, and/or spin. Alternatively, the ultrasound probe 200 may be initially oriented with a particular non-zero amount of tilt, rock, and/or spin. It should be understood that the initial orientation may depend on the particular circumstances of the application and/or the particular location on which the wearable device 100 is positioned on the subject.

Figure 8:
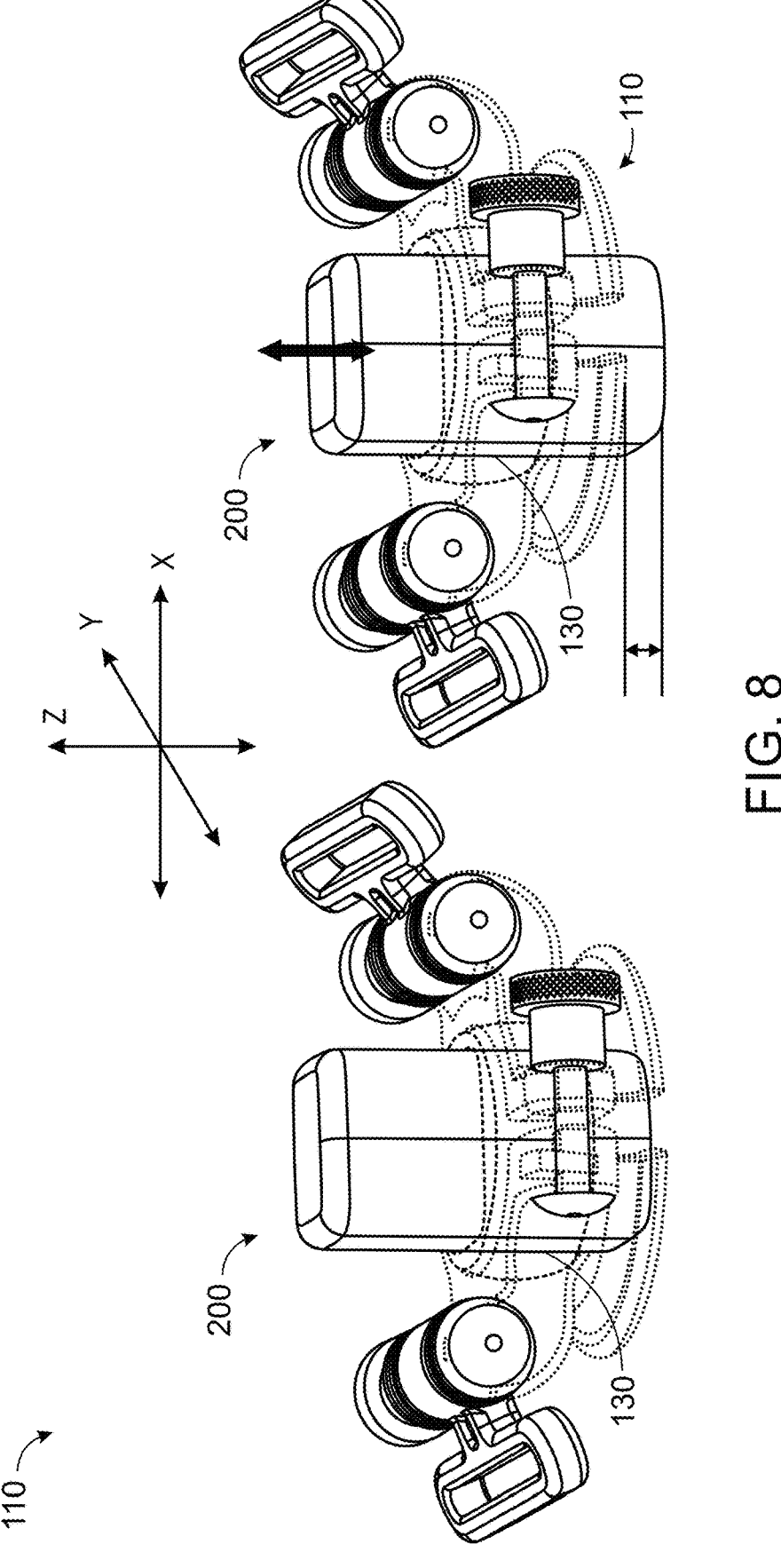
FIG. 8 is a diagram of positioning the ultrasound probe relative to the mount.

FIG. 8 is a diagram of positioning the ultrasound probe 200 relative to the mount 130. As shown in FIG. 8, the ultrasound probe 200 may be positioned at different positions relative to the mount 130. That is, the ultrasound probe 200 may be moved along the Z-axis to control an amount of contact and pressure between the ultrasound probe 200 and a surface of the subject. According to an embodiment, the wearable device 100 may be configured to permit a particular amount of movement of the ultrasound probe 200 along the Z-axis (e.g., 5 millimeters (mm), 10 mm, 15 mm, 20 mm, 30 mm, etc.). An operator may move the ultrasound probe 200 to a desired position and lock the position of the ultrasound probe 200 relative to the base 110 via the lock 150. The ultrasound probe 200 may include a substantially uniform cross section which may permit the ultrasound probe 200 to slide a variable amount into, and out of, the mount 130, thereby enabling a continuously variable amount of protrusion of the ultrasound probe 200 below the contact surface of the base 110. The variable protrusion may permit adaptation of the wearable device 100 to different body types and placement locations of the ultrasound probe 200.

Figure 9:
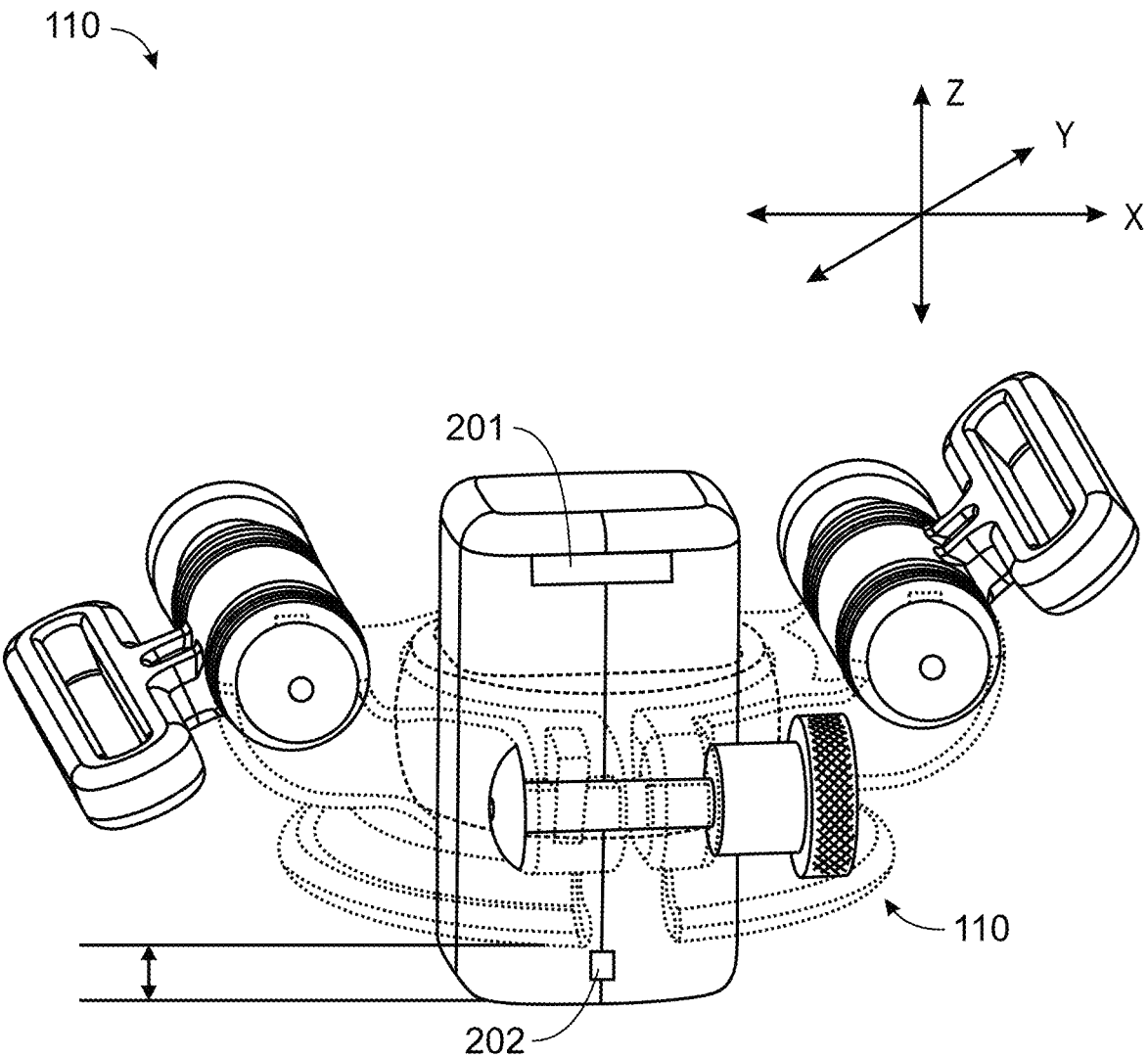
FIG. 9 is a diagram of stops provided on the ultrasound probe.

FIG. 9 is a diagram of a first stop 201 and a second stop 202 provided on the ultrasound probe 200. As shown in FIG. 9, the ultrasound probe 200 may include the first stop 201 and the second stop 202 that extend from the ultrasound probe 200. The first stop 201 and the second stop 202 may prevent movement of the ultrasound probe 200 beyond a particular position along the Z-axis. The wearable device 100 may be configured to permit increased probe protrusion for cardiac imaging applications. The ultrasound probe 200 may include additional stops provided on other sides or surfaces of the ultrasound probe 200 in other embodiments.

Figure 10:
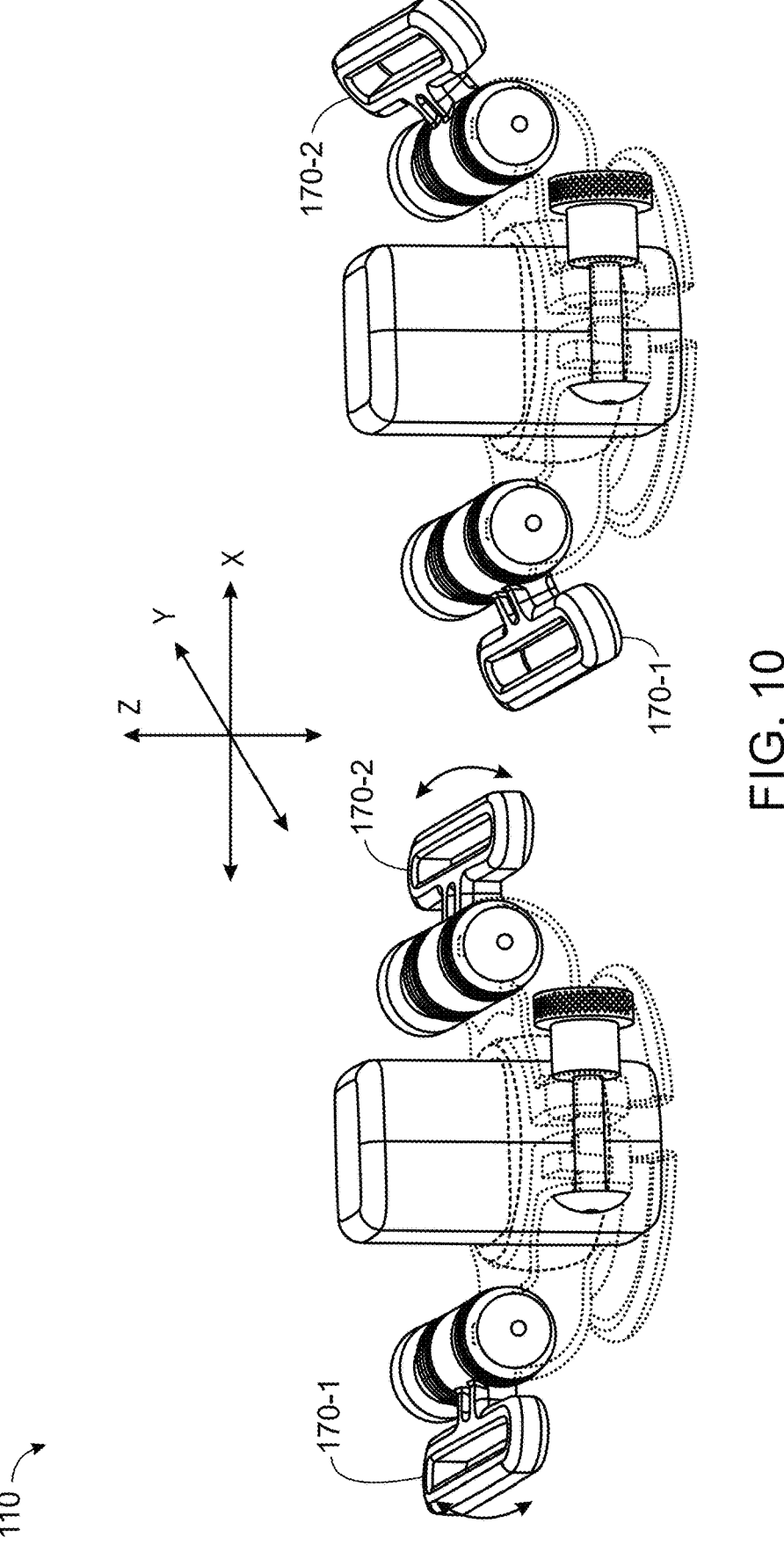
FIG. 10 is a diagram of locking the strap connectors at different angular positions relative to each other.

FIG. 10 is a diagram of locking the first strap connector 170-1 and the second strap connector 170-2 at different angular positions relative to each other. As shown in FIG. 10, the first strap connector 170-1 and the second strap connector 170-2 are independently adjustable relative to each other, such that the first strap connector 170-1 and the second strap connector 170-2 may be positioned, and locked, at the same angular position or different angular positions relative to each other and/or the base 110. An operator may lock the position of the first strap connector 170-1 relative to the base 110 via the first strap connector lock 190-1, and may lock the position of the second strap connector 170-2 relative to the base 110 via the second strap connector lock 190-2. Although the embodiments herein depict the wearable device 100 as including two independently adjustable strap connectors, it should be understood that other embodiments may include any other number of independently adjustable strap connectors, such as a single independently adjustable strap connector.

Figure 29:
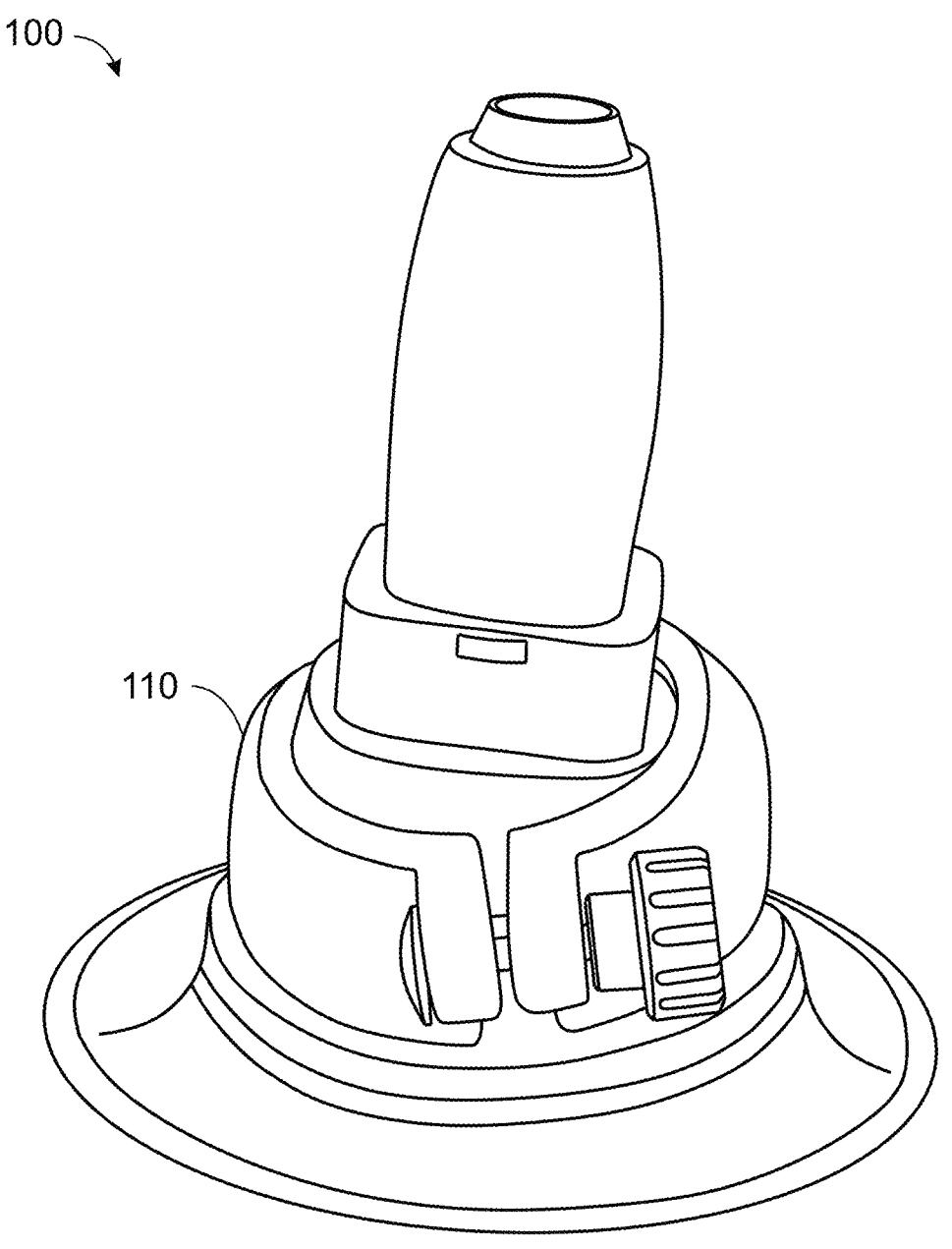
FIG. 29 is a diagram of a base that does not include strap connectors.

The wearable device 100 may include any number of strap connectors 170. For example, the wearable device 100 may include no strap connectors 170 (e.g., as shown in FIG. 29), a single strap connector 170, two strap connectors 170, three strap connectors 170, etc. Further, the wearable device 100 may include a particular number of strap connectors 170 that is based on the number of straps 300 to be used with the wearable device 100. As an example, if a single strap 300 is used with the wearable device 100, then the wearable device 100 may include two strap connectors 170. In some situations, the wearable device 100 may include more than a single strap 300. For example, a first strap 300 may be positioned substantially, or generally, horizontally with respect to the subject, and a second strap 300 may be positioned substantially, or generally, vertically with respect to the subject. As a particular example, the first strap 300 may be provided around a chest or abdomen of the subject, and the second strap 300 may be provided around a shoulder or the neck of the subject to further secure the wearable device 100 with respect to the subject. The number of straps 300 and/or strap connectors 170 might also be based on the particular application of the wearable device 100 and/or the location of usage of the wearable device 100. As an example, a medical imaging application in an intensive care unit might require less straps 300 to be used with the wearable device 100, whereas a cardiac monitoring application during ambulatory activities might require more straps 300 to be used with the wearable device 100.

The first strap connector 170-1 and the second strap connector 170-2 may be hingable and lockable to accommodate different body shapes and placement locations of the ultrasound probe 200. According to an embodiment, the first strap connector lock 190-1 and the second strap connector lock 190-2 may be Hirth couplings with fixed angular increments and a thumbscrew to compress the Hirth coupling, and may be configured to lock the angular positions of the first strap connector 170-1 and the second strap connector 170-2, respectively. With the angled first strap connector 170-1 and the angled second strap connector 170-2, the attached strap 300 may be oriented to translate the belt tension force into resulting angular forces or down forces on the base 110 of the wearable device 100 causing the wearable device 100 to align with contoured anatomic locations of the subject. This feature may increase the stability of the wearable device 100 and the ultrasound probe 200 and adaptability to various body shapes and locations of the ultrasound probe 200. Additionally, when the first strap connector 170-1 and the second strap connector 170-2 are angled in the upward position, added down-force is realized at the surface of the ultrasound probe 200 for scans that might require compression of surface tissue to realize a desired ultrasound image. Alternatively, the first strap connector 170-1 and the second strap connector 170-2 may be fixed in position with a design that accommodates substantially most of the subject population.

According to an embodiment, a wearable device 100 may be associated with a unique identifier (e.g., a stock keeping unit (SKU), a device identifier, a manufacturer identifier, or the like). A particular unique identifier (e.g., a particular SKU) may be associated with a particular number of strap connectors 170, a particular orientation and/or a particular geometry of the strap connectors 170, a particular type of strap connector 170, a particular orientation of the mount 130 with respect to the base 110, a particular amount of protrusion of the ultrasound probe 200 with respect to the mount 130, or the like.

According to an embodiment, a particular anatomical location may be associated with a particular unique identifier (e.g., SKU) of a wearable device 100. For example, the chest may be associated with a first unique identifier (e.g., SKU), the abdomen may be associated with a second unique identifier (e.g., SKU), etc. According to another embodiment, a particular anatomical location and a particular application may be associated with a particular unique identifier (e.g., SKU). For example, cardiac monitoring may be associated with a first unique identifier (e.g., SKU), abdominal imaging may be associated with a second unique identifier (e.g., SKU), etc. According to another embodiment, a particular anatomical location and a particular application may be associated with a set of unique identifiers (e.g., SKUs). For example, a first unique identifier (e.g., SKU) of a wearable device 100 for cardiac monitoring may be associated with a wearable device 100 having a first orientation of the strap connectors 170, a second unique identifier (e.g., SKU) of a wearable device 100 for cardiac monitoring may be associated with a wearable device 100 having a second orientation of the strap connectors 170, etc. A medical personnel may select a particular unique identifier (e.g., SKU) of a wearable device 100 for a subject based on a body geometry of the subject, based on the placement location of the wearable device 100, based on the application, or the like.

Figure 11:
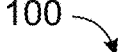
FIG. 11 is a diagram of the wearable device being positioned on a subject with the strap connectors being locked at different angular positions relative to each other.
Figure 11:
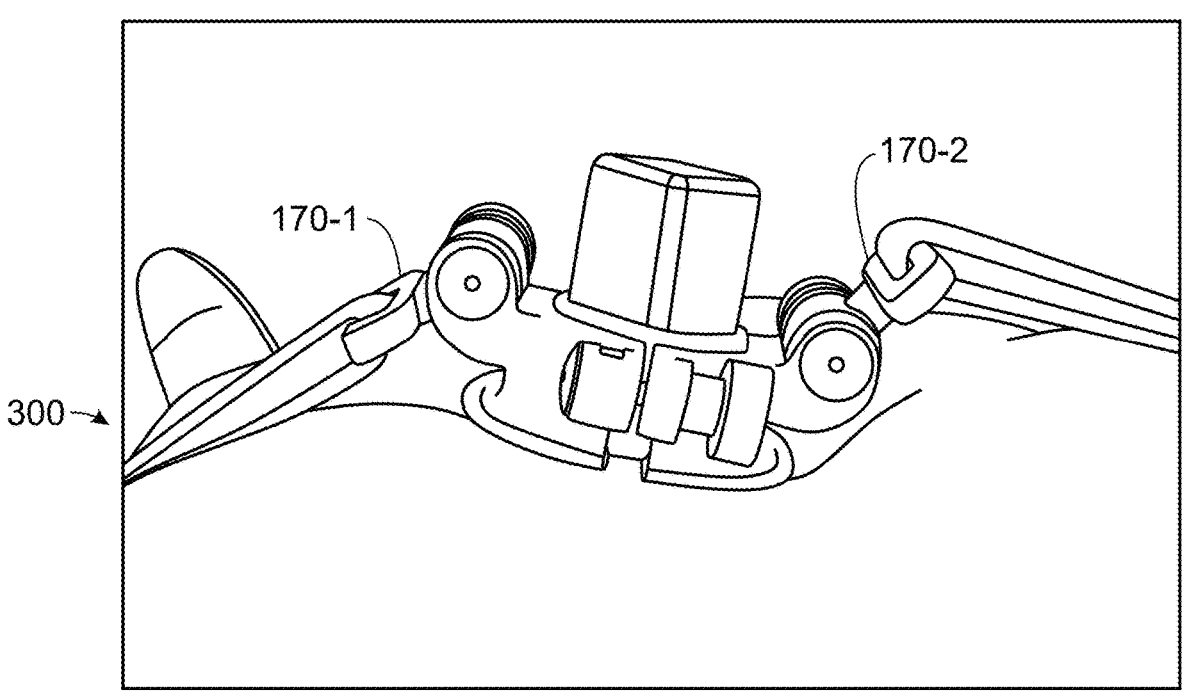

FIG. 11 is a diagram of the wearable device 100 being positioned on a subject with the first strap connector 170-1 and the second strap connector 170-2 being locked at different angular positions relative to each other. As shown in FIG. 11, the positioning of the first strap connector 170-1 and the second strap connector 170-2 permits improved contact of the wearable device 100 relative to a non-uniform surface of the subject and permits improved contact between the ultrasound probe 200 and the surface of the subject. According to an embodiment, such as, for example, for improved stability and positioning on the parasternal window during cardiac imaging, the second strap connector 170-2 may be angled higher than the first strap connector 170-1 in order to compensate for the tilted position of the base 110 on the chest of the subject. This configuration may provide for a substantial reduction in the degree of misalignment between the subject and the base 110.

Figure 12:
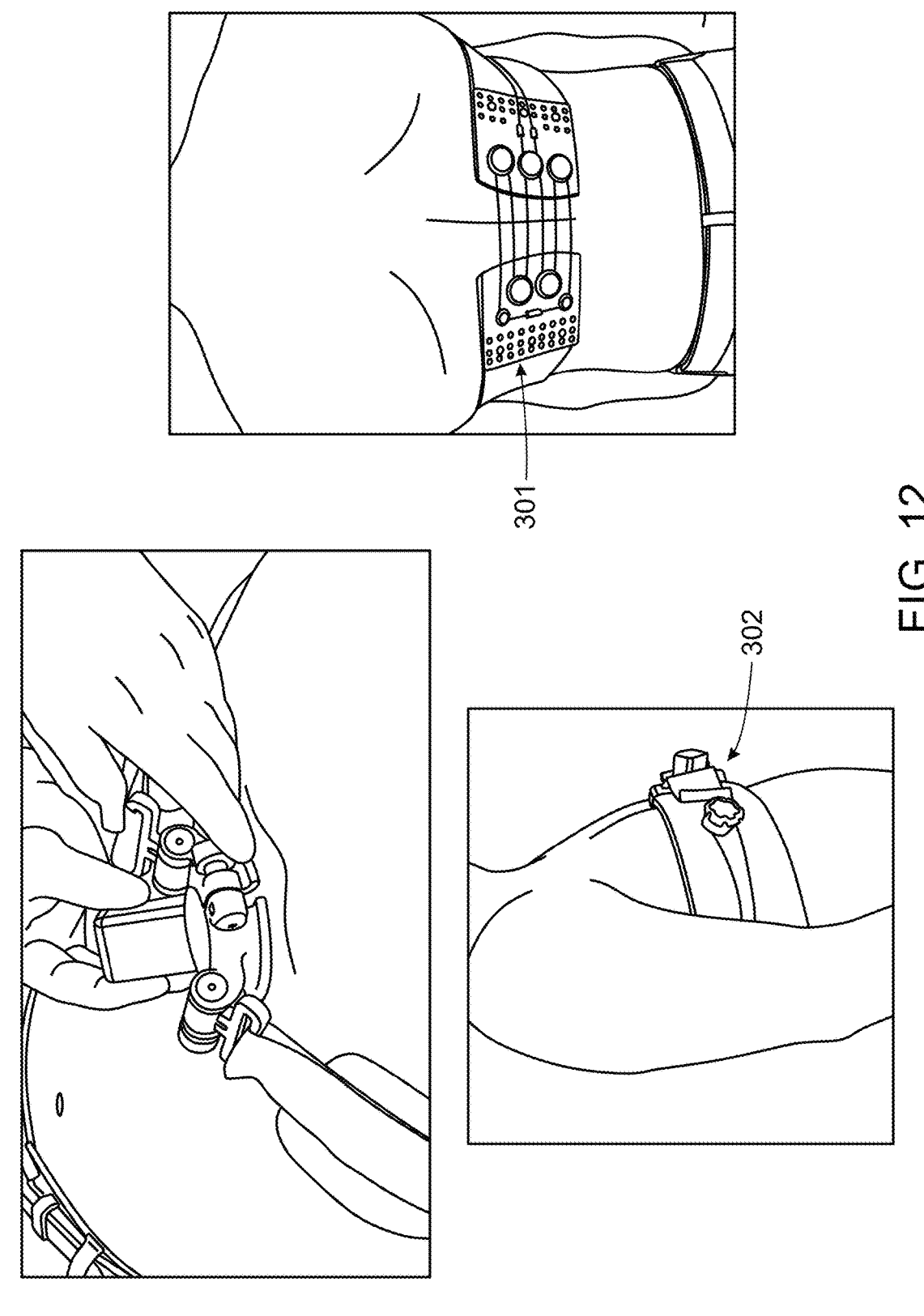
FIG. 12 is a diagram of locking the ultrasound probe relative to the base of the wearable device, and locking the wearable device to a subject via the strap.

FIG. 12 is a diagram of locking the ultrasound probe 200 relative to the base 110 of the wearable device 100, and locking the wearable device 100 to a subject via the strap 300. As shown in FIG. 12, an operator may manipulate the ultrasound probe 200 to orient the ultrasound probe 200 relative to the base 110, and lock the orientation of the ultrasound probe 200 relative to the base 110 via the lock 150. The operator may then fasten the strap 300 to the subject via laces 301 and a rotary mechanism 302. The adjustable strap 300 may hold the wearable device 100 securely on the subject. The strap 300 may have a Velcro section for an initial and rapid adjustment of circumferential sizing, and the laces 301 and the rotary mechanism 302 which give the operator control over the final tension of the strap 300. The laces 301 may ratchet as the rotary mechanism 302 is turned, and may have a tension locking feature that is engaged or disengaged by manipulating the rotary mechanism 302. The strap 300 may be comprised of a material which accommodates a certain amount of stretch, and may have features which increase friction between the strap 300 and surface of the subject such as silicone dots, silicone strips, or the like. In the case of the ultrasound probe 200 being wired, the strap 300 may include fixtures for managing the cable of the ultrasound probe 200 and preventing inadvertent cable pulls from impacting the alignment of the ultrasound probe 200 relative to the subject. Although FIG. 12 depicts a particular configuration of the strap 300, it should be understood that other embodiments may include different configurations of the strap 300. For instance, in some embodiments, the strap 300 may include less features, more features, or different features than as depicted in FIG. 12. In other words, the strap 300 may be more elaborate, less elaborate, more complex, less complex, or the like, depending on the particular application of the wearable device 100.

Figure 13:
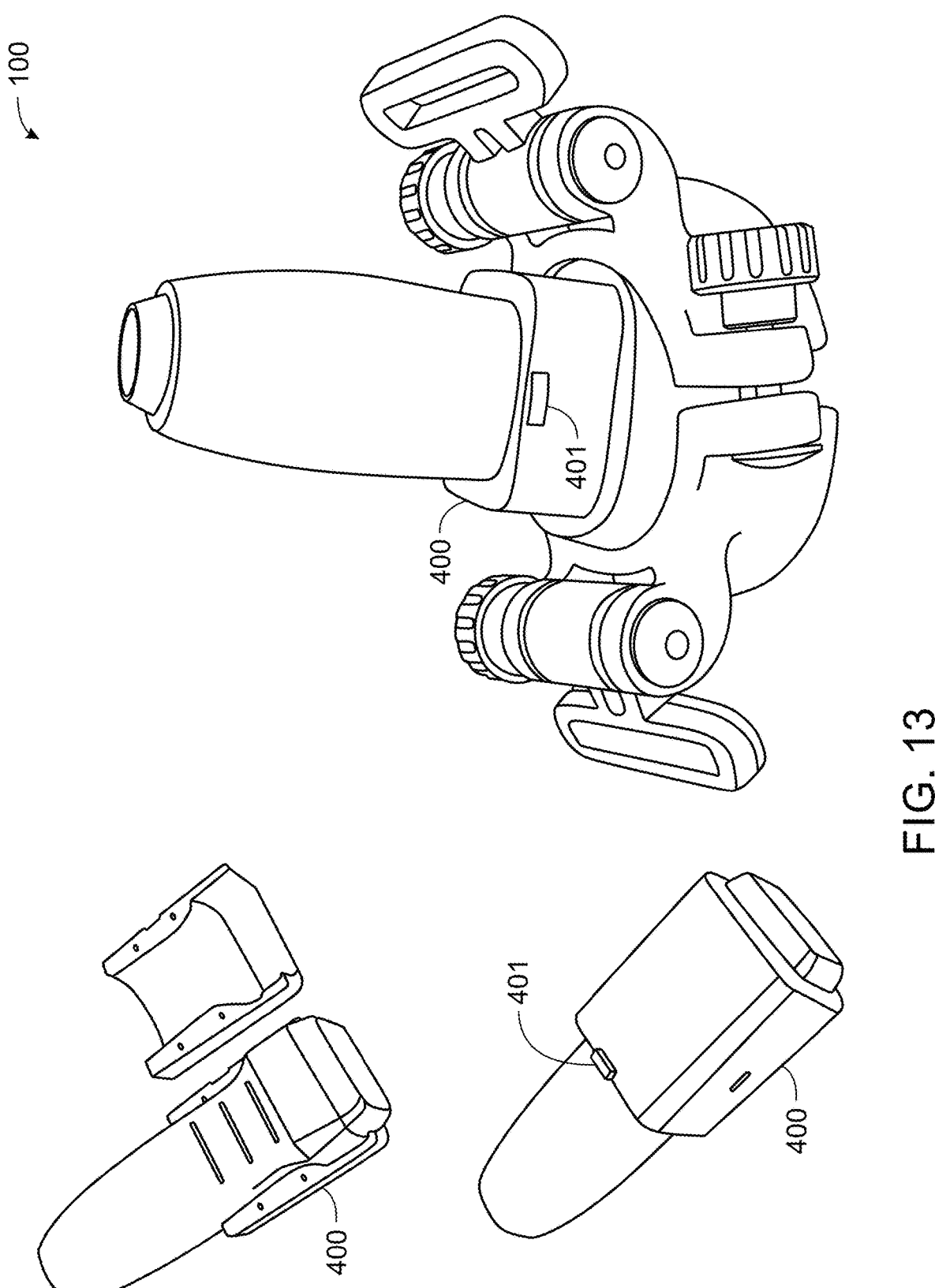
FIG. 13 is a diagram of an adapter for the ultrasound probe.

FIG. 13 is a diagram of an adapter 400 for the ultrasound probe 200. The adapter 400 is configured to attach to the ultrasound probe 200. The adapter 400 may be configured to attach to a specific type of ultrasound probe 200, and may standardize an outer diameter for interfacing with the mount 130. The adapter 400 may include a stop 401 that prevents the adapter 400 from moving beyond a particular position along the Z-axis. The adapter 400 may be used for ultrasound probes 200 that do not have a uniform cross section. In these cases, the adapter 400 may convert the outer housing of the ultrasound probe 200 to a uniform cross section to enable variable protrusion with respect to the mount 130. The wearable device 100 may include a handle that may be used with ultrasound probes 200 that are ultra low-profile. The handle may be foldable, stowable, removable, or the like. The handle may be used during positioning of the ultrasound probe 200, and folded, stowed, or removed, when the positioning process is complete. Alternatively, one or more features in the housing of the low-profile ultrasound probe 200, such as a small depression, could be configured to allow a finger of the operator to manipulate the orientation of the ultrasound probe 200. The adapter 400 may not be necessary in some situations. For example, some ultrasound probes 200 may be configured for interfacing directly with the mount 130, and/or may include a substantially uniform housing. In these cases, the ultrasound probe 200 may directly interface with the mount 130 without the need for the adapter 400 because the housing of the ultrasound probe 200 includes a relatively comparable shape as the opening 132 of the mount 130. The adapter 400 may be applicable to instances where the ultrasound probe 200 was not configured for interfacing directly with the mount 130, and/or does not include a substantially uniform housing. In these cases, the adapter 400 may provide an outer surface that includes a relatively comparable shape as the opening 132 of the mount 130.

Figure 14:
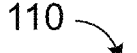
FIG. 14 is a diagram of an adhesive provided on the base and an acoustic coupling pad provided on the ultrasound probe.
Figure 14:
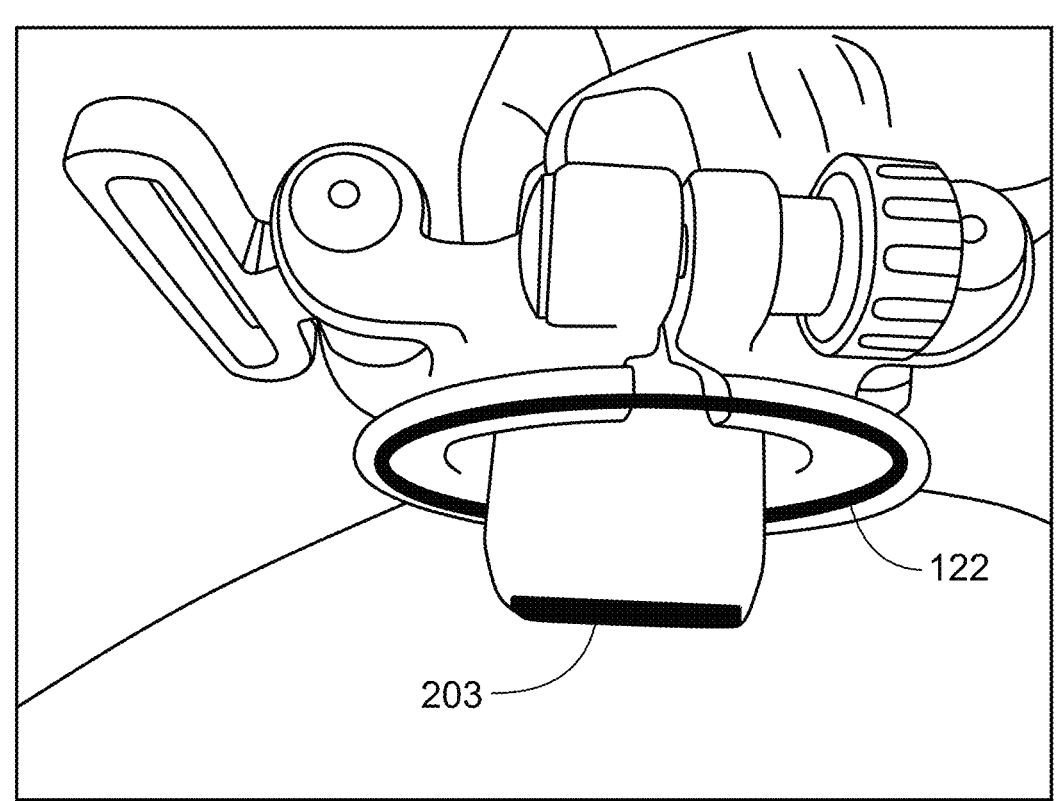

FIG. 14 is a diagram of an adhesive 122 provided on the base 110 and an acoustic coupling pad 203 provided on the ultrasound probe 200. As shown, the adhesive 122 may be provided on a bottom surface of the bottom portion 111 of the base 110. The adhesive 122 may stabilize the base 110 on the surface of the subject, and stabilize the ultrasound probe 200 with respect to the subject. The acoustic coupling pad 203 may be a hydrogel pad, a gel pad, or the like. The acoustic coupling pad 203 may permit movement of the ultrasound probe 200 along the surface of the subject while the ultrasound probe 200 is being positioned, and may improve acoustic coupling between the ultrasound probe 200 and the subject.

Figure 15:
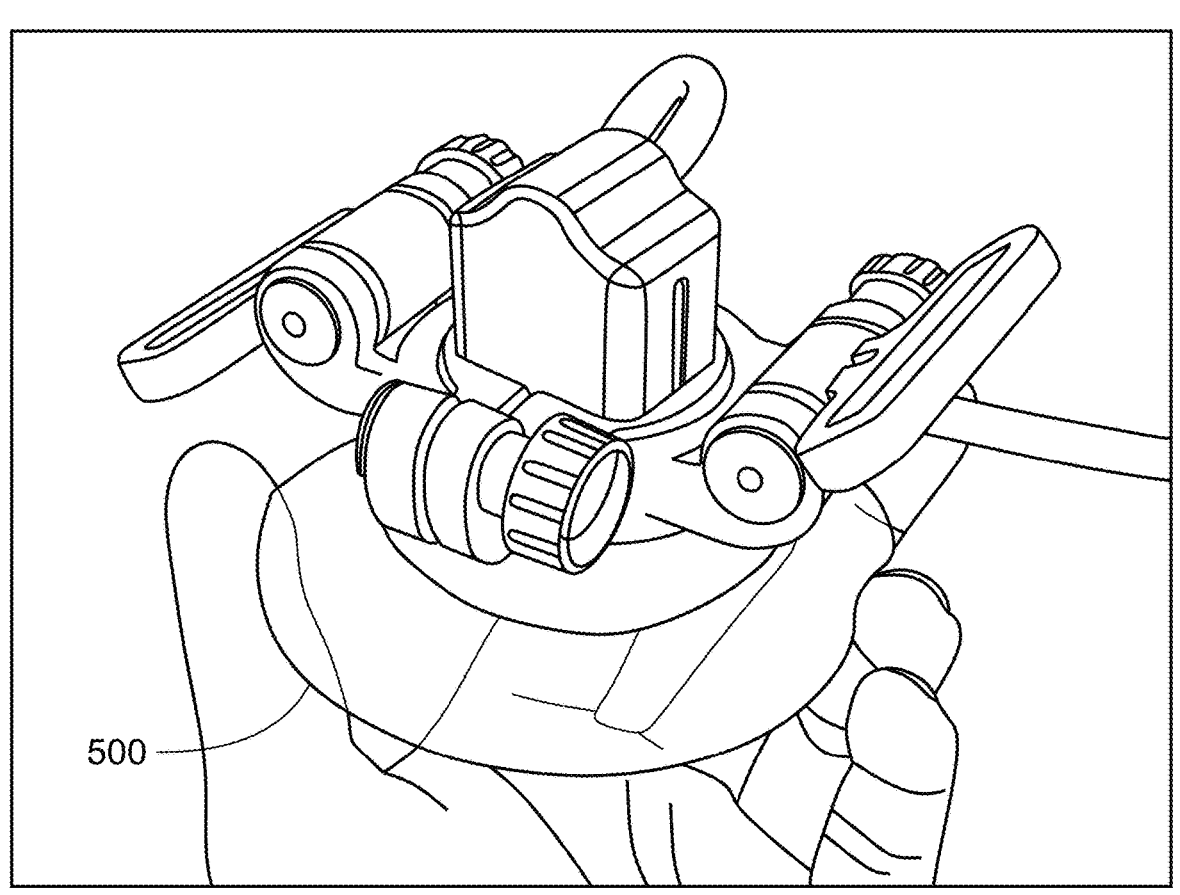
FIG. 15 is a diagram of a cup provided on the wearable device.
Figure 16:
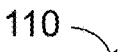
FIG. 16 is a diagram of the cup being positioned on the subject.
Figure 16:
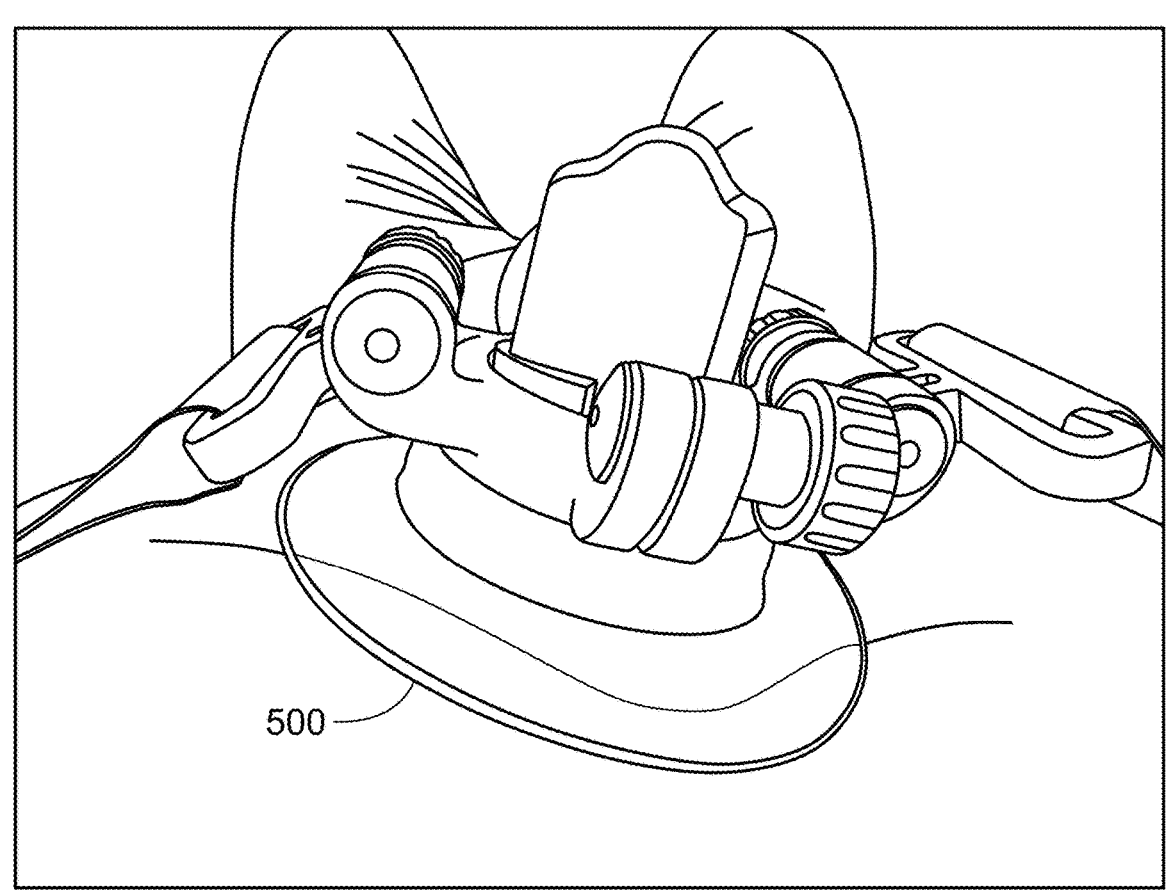

FIG. 15 is a diagram of a cup 500, and FIG. 16 is a diagram of the cup 500 being positioned on the subject. The cup 500 may be a swappable surface contact component that removably attaches to the base 110. The cup 500 may be comprised of any suitable material. For example, the cup 500 may be comprised of a biocompatible, compliant, flexible, and/or elastic material, which permits stabilization of the wearable device 100 on the subject, improves conformability to the subject, increases subject comfort, or the like. As particular examples, the cup 500 may be comprised of silicone, thermoplastic polyurethane, thermoplastic elastomer, rubber, or the like. The cup 500 may be fabricated in multiple sizes and shapes which suit different body types. The cup 500 might not be rotationally symmetric in some embodiments. In order to suit different body shapes, some areas on the cup 500 may be thickened or protrude further from the base 110 than other areas. With the natural tackiness of the cup 500 on the surface of the subject and the resulting stability of the wearable device 100, additional adhesive might not be required in order to install the wearable device 100 on the subject, thereby improving workflow efficiency. The cup 500 may be conformable, and may be configured to conform to the contours of the subject and stabilize the ultrasound probe 200. The larger surface area of the cup 500 may increase friction and stability. In order to ensure a precise fit to a wide array of body shapes and/or probe placement locations, a custom cup 500 may be molded for specific individuals. This process may include a quick three dimensional body profile scan which is uploaded and then converted to a three-dimensional (3D) data file. This body contour map is used to inform the design of a 3D printed silicone cup mold. The outer flange of the cup 500 may therefore be configured to conform to subject-specific anatomy.

Figure 17:
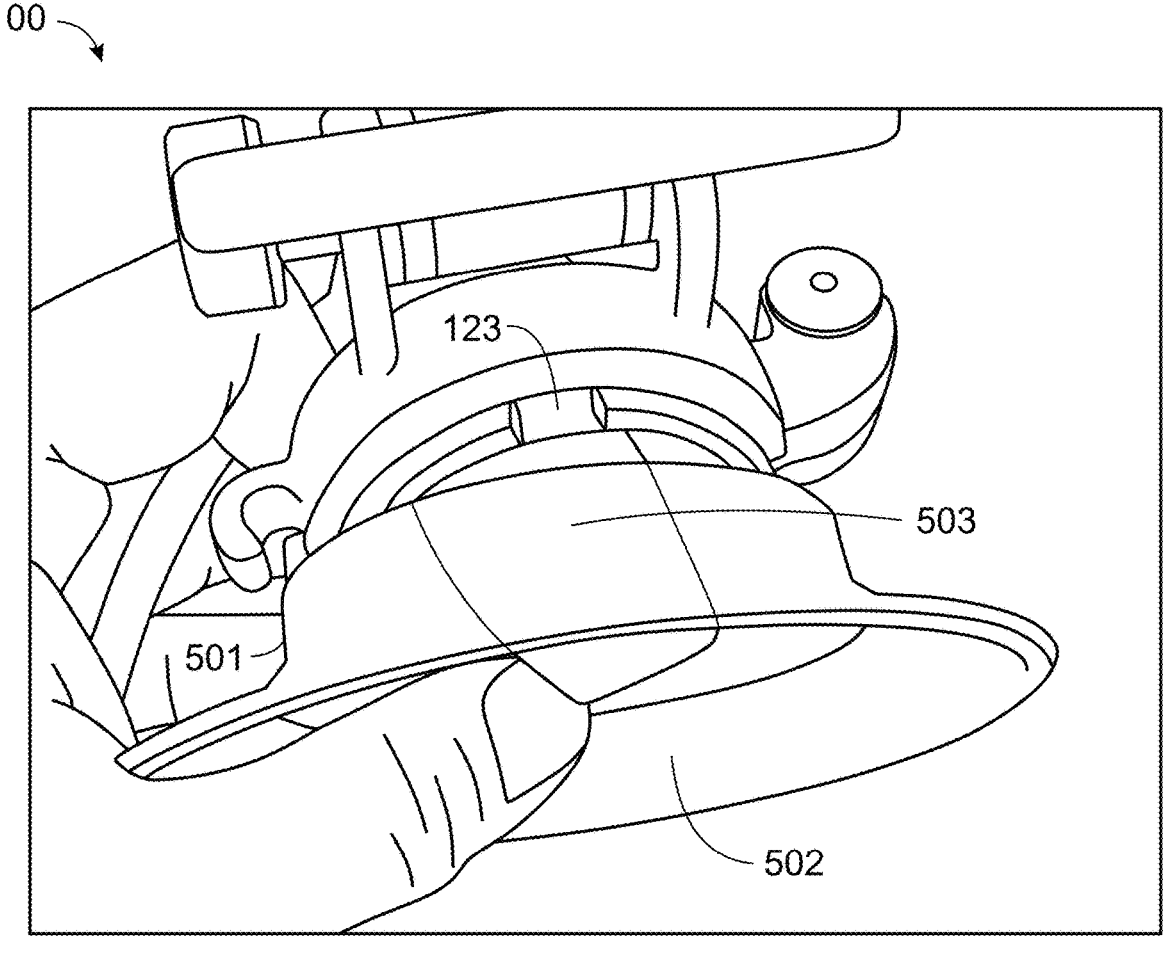
FIG. 17 is a diagram of the cup interfacing with the base.

FIG. 17 is a diagram of the cup 500 interfacing with the base 110. The cup 500 may have a top portion 501 that interfaces with the base 110, a bottom portion 502 that contacts a surface of the subject, and a keyed feature 503 on an internal surface of the cup 500 that interfaces with a keyed feature 123 of the base 110 to lock the orientation of the cup 500 relative to the base 110 and prevent unwanted rotation. The cup 500 may be fabricated as a single patient disposable that is replaced between imaging sessions or the cup 500 may be a durable material that is cleaned and sterilized between uses. The bottom portion 502 of the cup may have a fine surface finish. The surface finish on the cup 500 may be highly polished to increase tackiness and increase friction against skin due to the molecular interactions between the material of the bottom portion 502 and skin, thereby increasing stability when the cup 500 contacts the surface of the subject. The cup 500 may have a removable liner that may protect the surface finish of the bottom portion 502. The shape of the cup 500 may be circular in profile or the shape may be non-symmetrical to allow greater range of angular motion for the ultrasound probe 200 or to accommodate ultrasound probes 200 of different shapes. The shape may also include radial slits to enable different areas of the cup 500 to move independently over large asperities in subject anatomy and effectively lower the stiffness of the cup 500.

Figure 18:
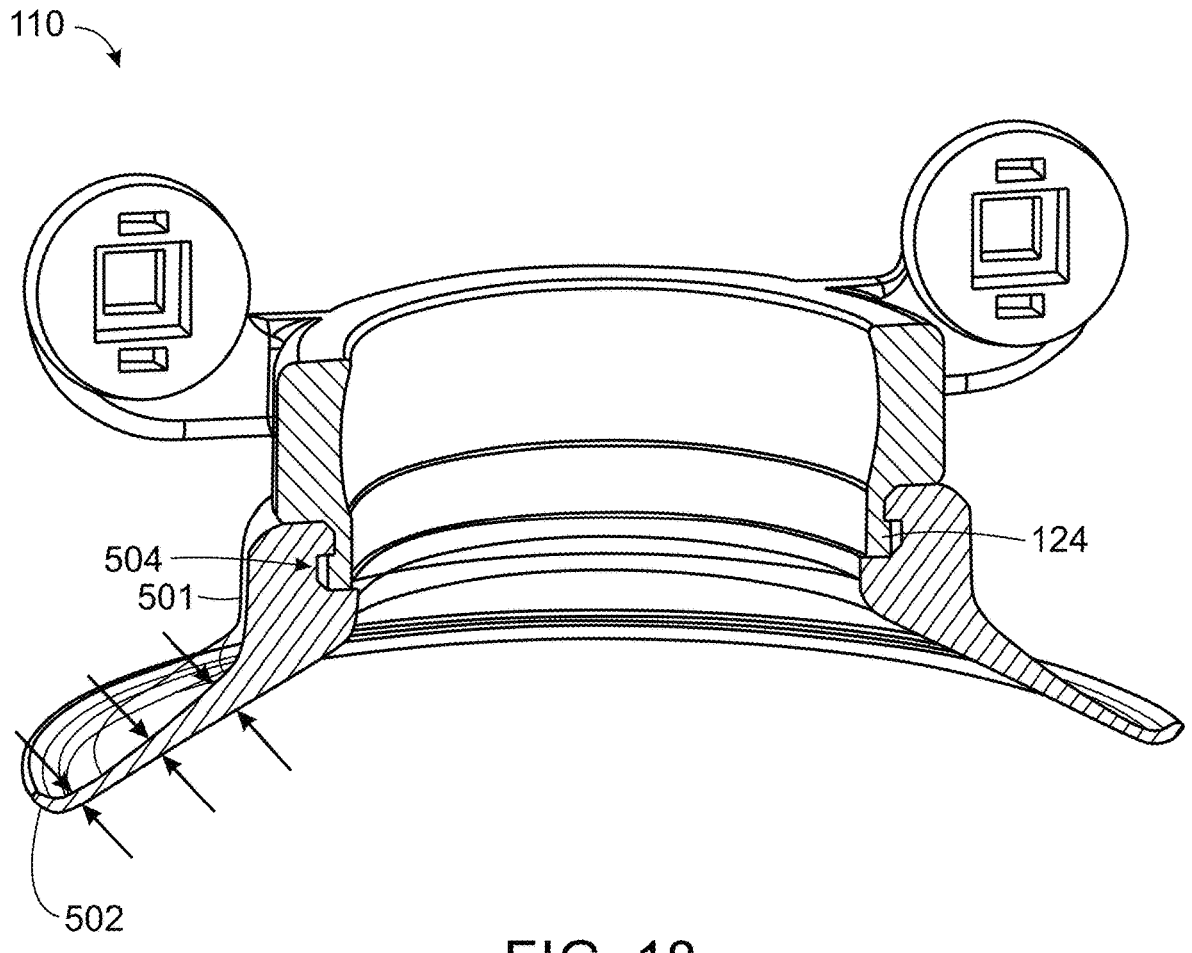
FIG. 18 is a diagram of a cross section of the base and the cup.

FIG. 18 is a diagram of a cross section of the base 110 and the cup 500. As shown in FIG. 18, the cup 500 may have a tapered bell shape which gradually thins towards the end of the cup 500, thereby reducing rigidity and increasing subject comfort. The cup 500 may include a recess 504 that interfaces with a protrusion 124 of the base 110 to lock the cup 500 and the base 110.

Figure 19:
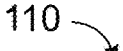
FIG. 19 is a diagram of an integrated cable hook that secures the cable of the ultrasound probe to the base.
Figure 19:
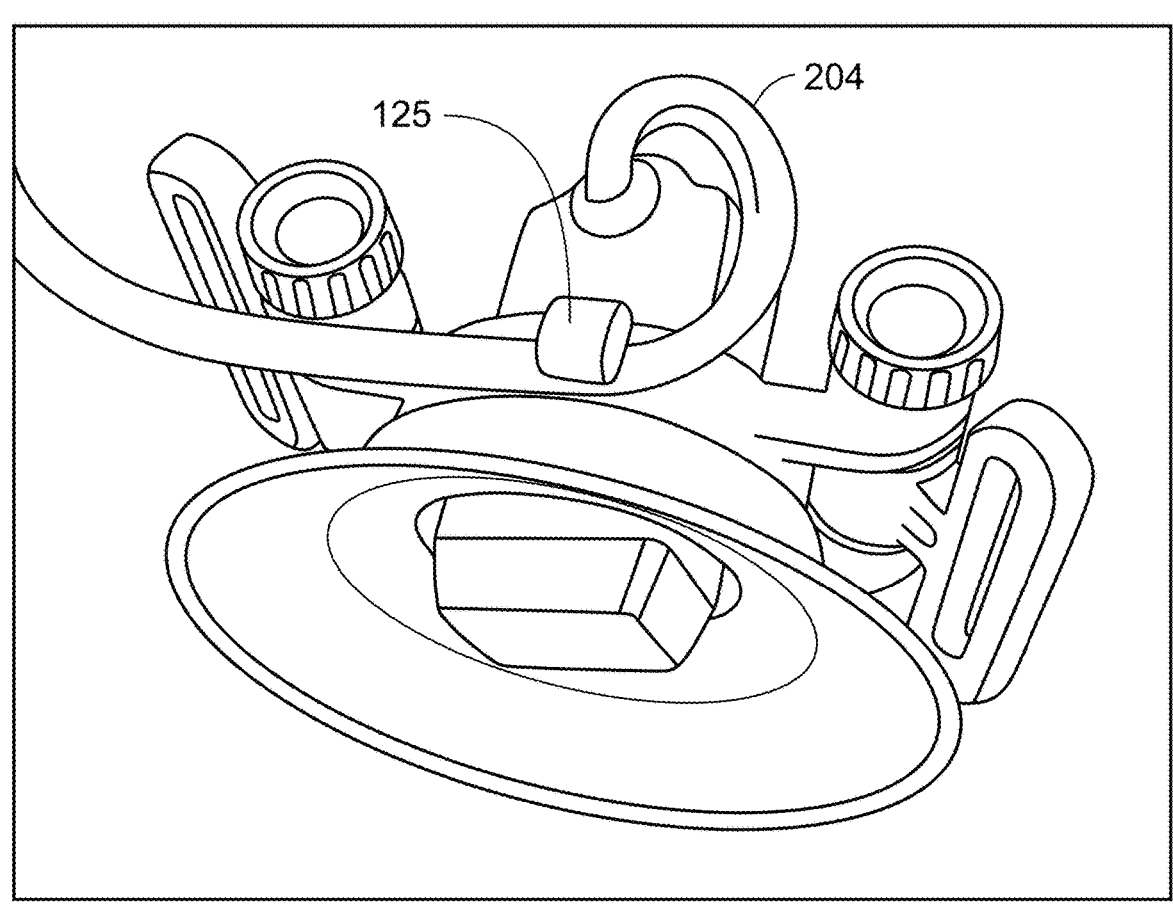

FIG. 19 is a diagram of an integrated cable hook 125 that secures the cable 204 of the ultrasound probe 200 to the base 110. The cable hook 125 may act as a strain relief, thereby preventing unintentional displacement of the ultrasound probe 200 when the cable is pulled.

Figure 20:
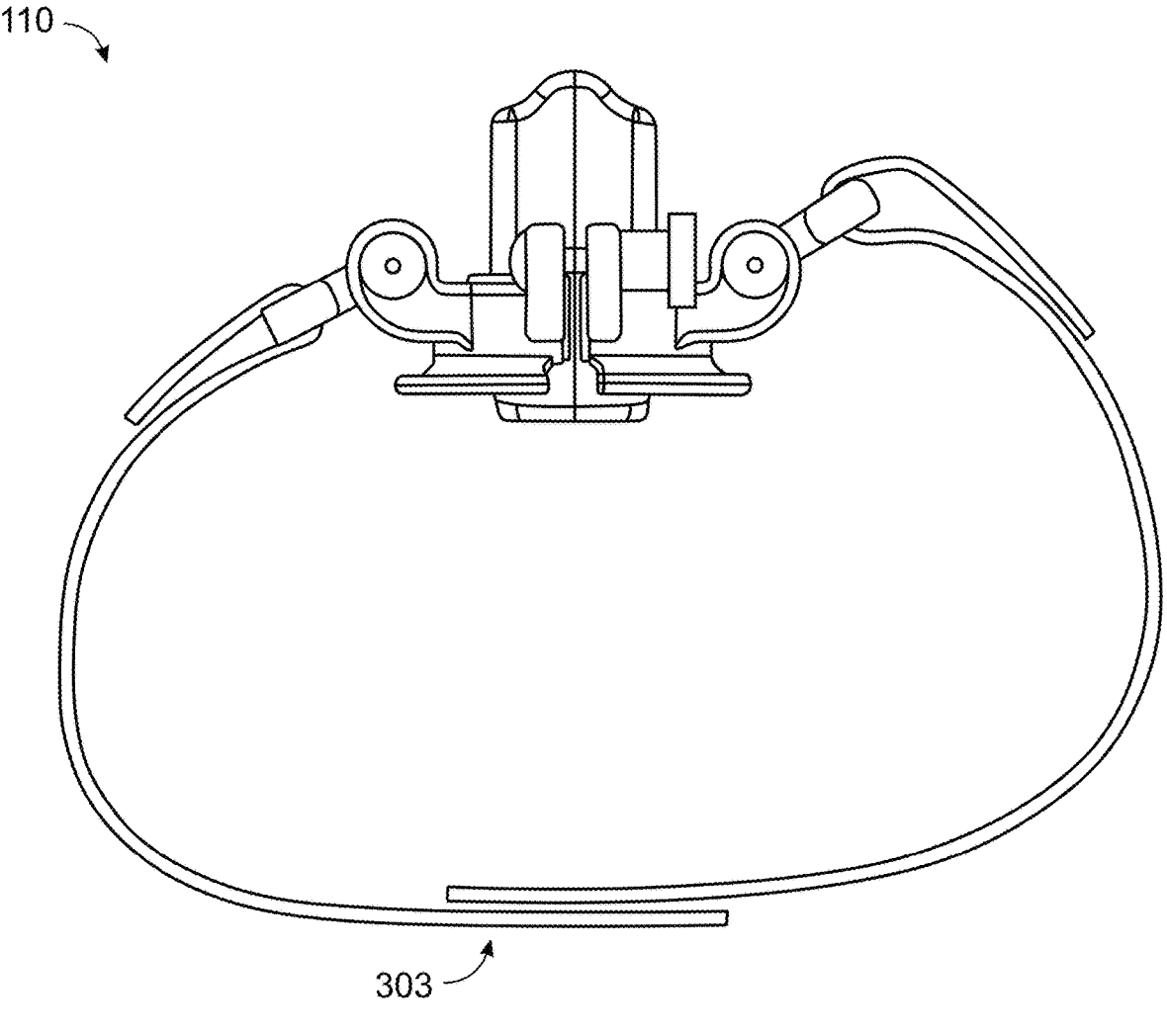
FIG. 20 is a diagram of the strap.

FIG. 20 is a diagram of the strap 300. The strap 300 may include a break 303 in the strap 300 on the backside of the subject which allows the strap 300 to be easily wrapped around the subject and fastened while the subject is temporarily positioned upright and/or leaned forward to obtain a macro fit. The laces 301 and the rotary mechanism 302 may enable finer tuning of the fit. Although FIG. 20 depicts a particular configuration of the strap 300, it should be understood that other embodiments may include different configurations of the strap 300. For instance, in some embodiments, the strap 300 may include less features, more features, or different features than as depicted in FIG. 20. As an example, in an embodiment, the strap 300 may be a single continuous material that is fastened to the wearable device 100 by passing the strap 300 through the strap connectors 170, pulling the strap 300 tight, and attaching an end of the strap 300 to the body of the strap 300 via Velcro.

Figure 21:
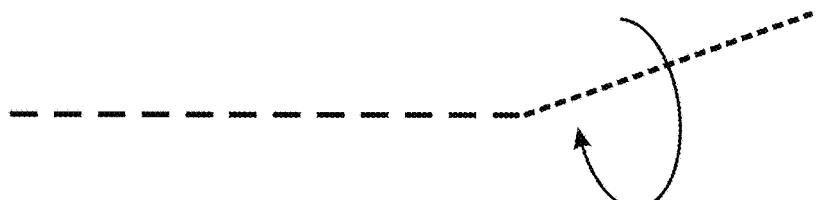
FIG. 21 is a diagram of the cup and the base.
Figure 21:
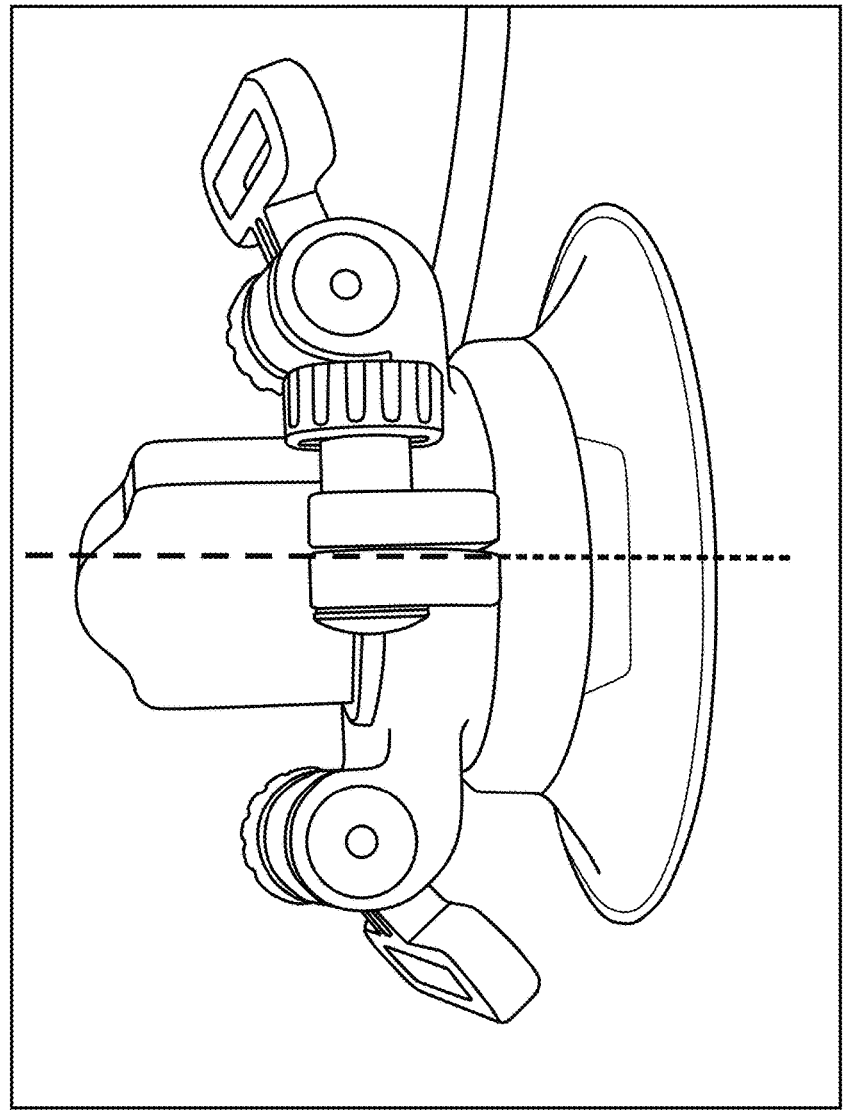

FIG. 21 is a diagram of the cup 500 and the base 110. The cup 500 and the base 110 may be aligned as shown in FIG. 12. Alternatively, the cup 500 and the base 110 may have a fixed or variable angle in order to accommodate different body shapes. In addition, the angle could be rotatable, and lockable, about the center axis so that the angle could be oriented to a position which suits the subject.

Figure 22:
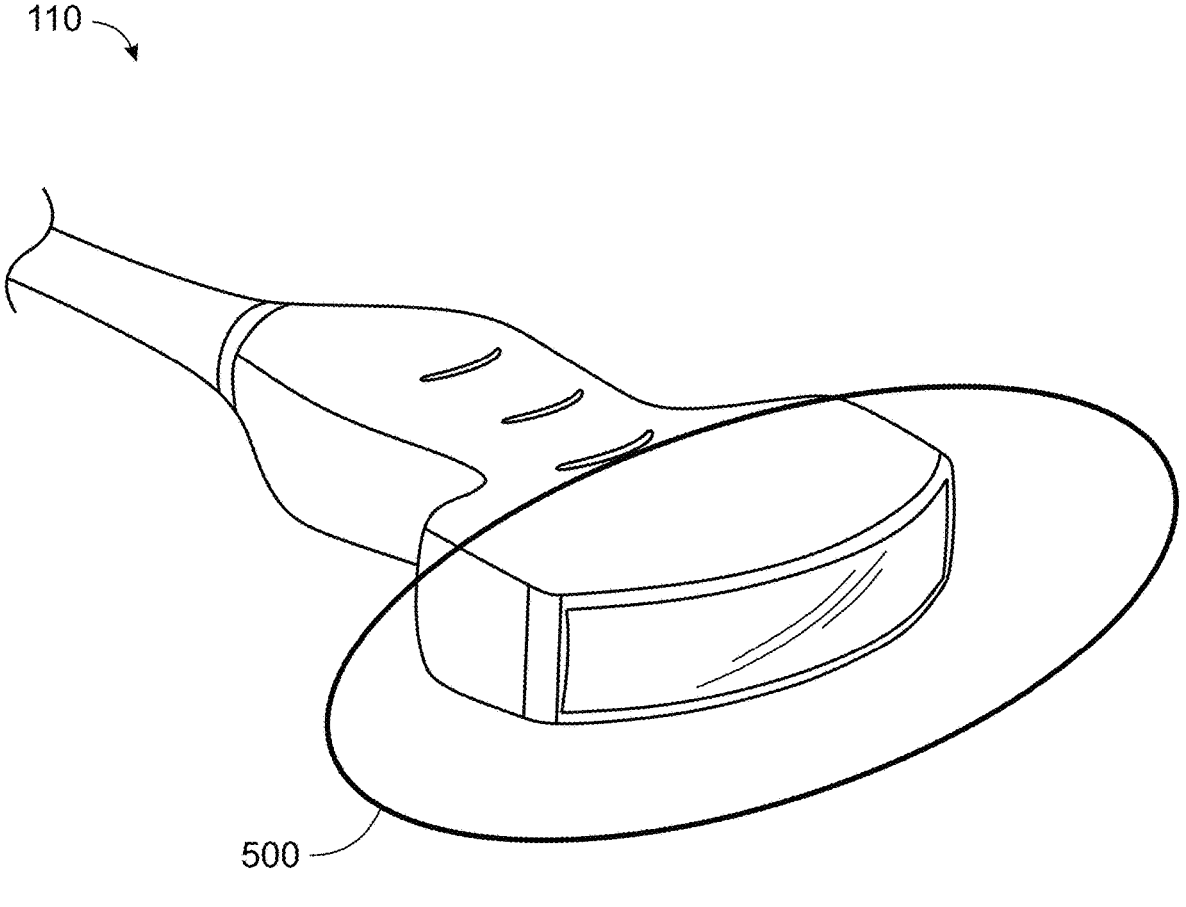
FIG. 22 is a diagram of the cup having an elliptical geometry.

FIG. 22 is a diagram of the cup 500 having an elliptical geometry. The cup 500 may be fabricated in multiple sizes and shapes to suit varying geometries of the ultrasound probes 200. For example, for larger linear or curved-linear ultrasound probes 200, the cup 500 may be fabricated as an elliptical shape as shown in FIG. 22.

Figure 23:
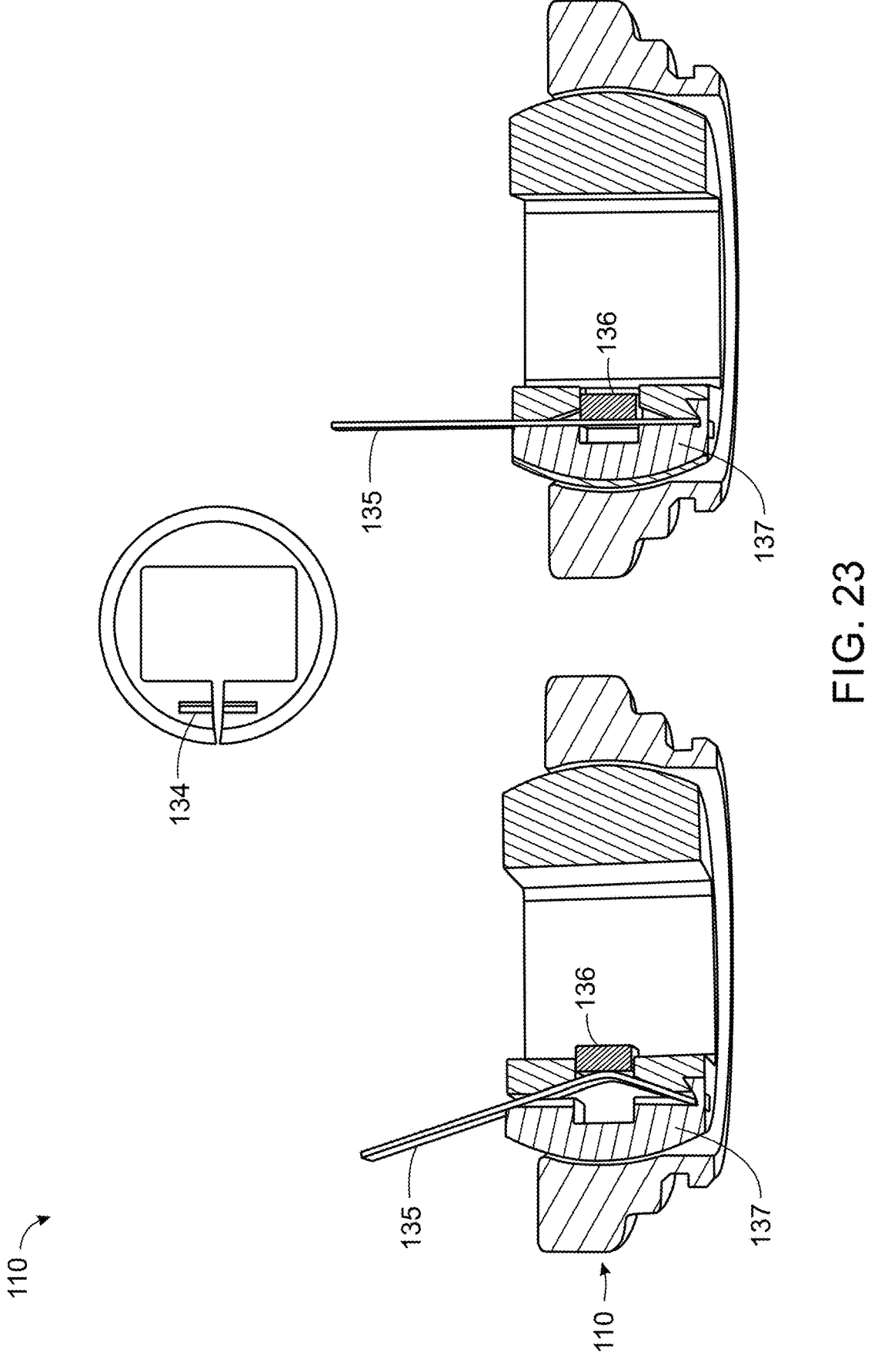
FIG. 23 is a diagram of a locking mechanism of the mount.

FIG. 23 is a diagram of a locking mechanism of the mount 130. As shown in FIG. 23, the locking mechanism may include a slot 134, a spring 135, a lock 136, and a wedge 137. The locking mechanism may be a single-action locking mechanism to both lock the orientation of the ultrasound probe 200 relative to the base 110 and the position of the ultrasound probe 200 relative to the mount 130. In this embodiment, the base 110 may be of a fixed diameter and might not include the lock 150. An interference fit may be provided by increasing the diameter of the mount 130 by driving the wedge 137 into the slot 134. To effect this change in diameter without also losing grip on the ultrasound probe 200, the spring 135 may have two points of contact with the wedge 137 and a point of contact with the lock 136 which is compressed into the opening 132 in the locked configuration.

Figure 24:
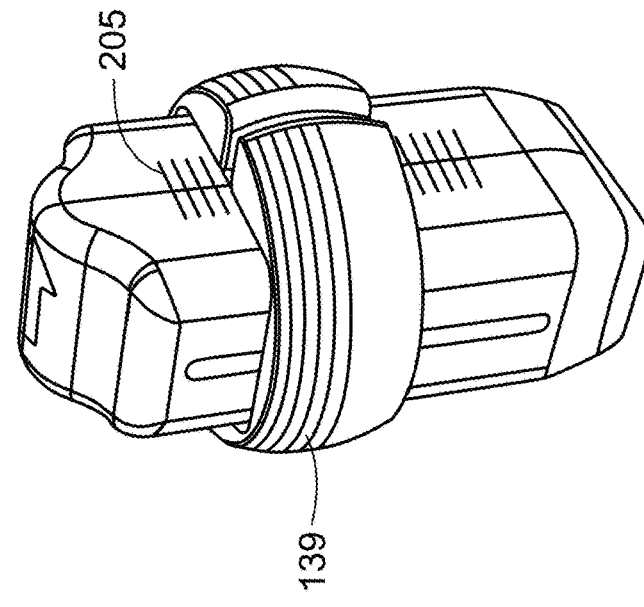
FIG. 24 is a diagram of fiducial markings.
Figure 24:
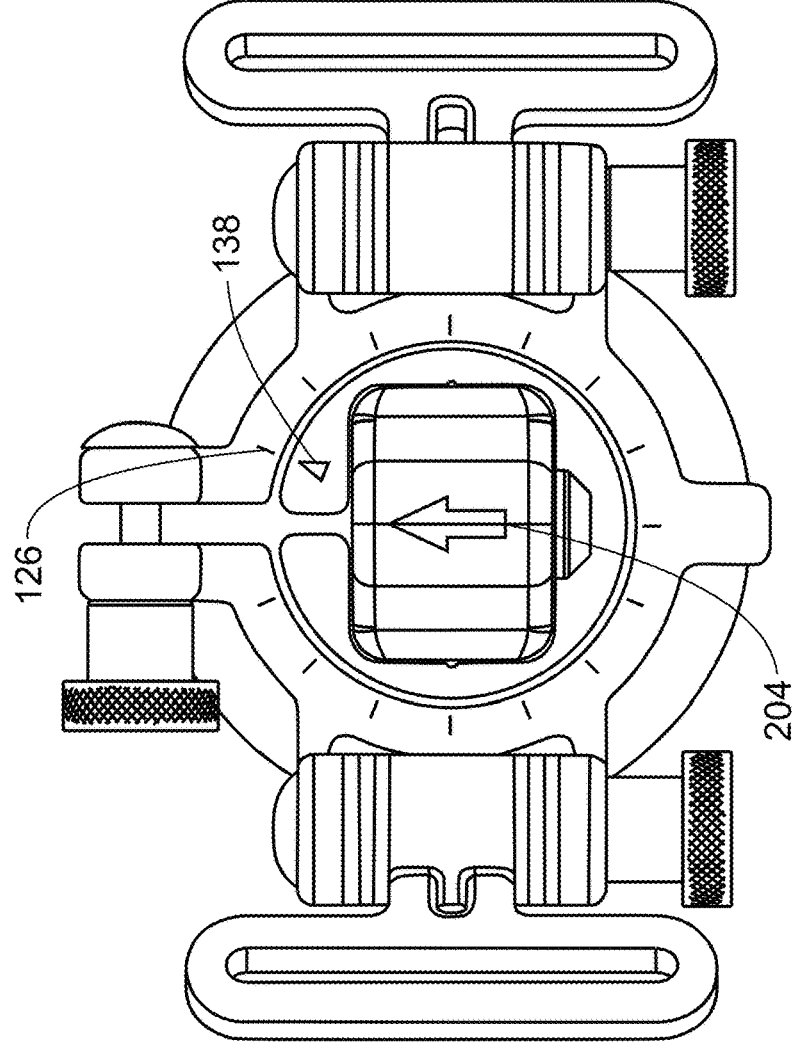

FIG. 24 is a diagram of fiducial markings. As shown in FIG. 24, the base 110 may include rotational fiducial markings 126, the mount 130 may include a rotational fiducial indicator 138 and rotational fiducial markings 139, and the ultrasound probe 200 may include an orientation fiducial marking 204 and vertical fiducial markings 205. The fiducial markings enable reproducibility for specific patients and allow operators to pre-set the angle and position of the ultrasound probe 200 before placing the wearable device 100 on the subject.

Figure 25:
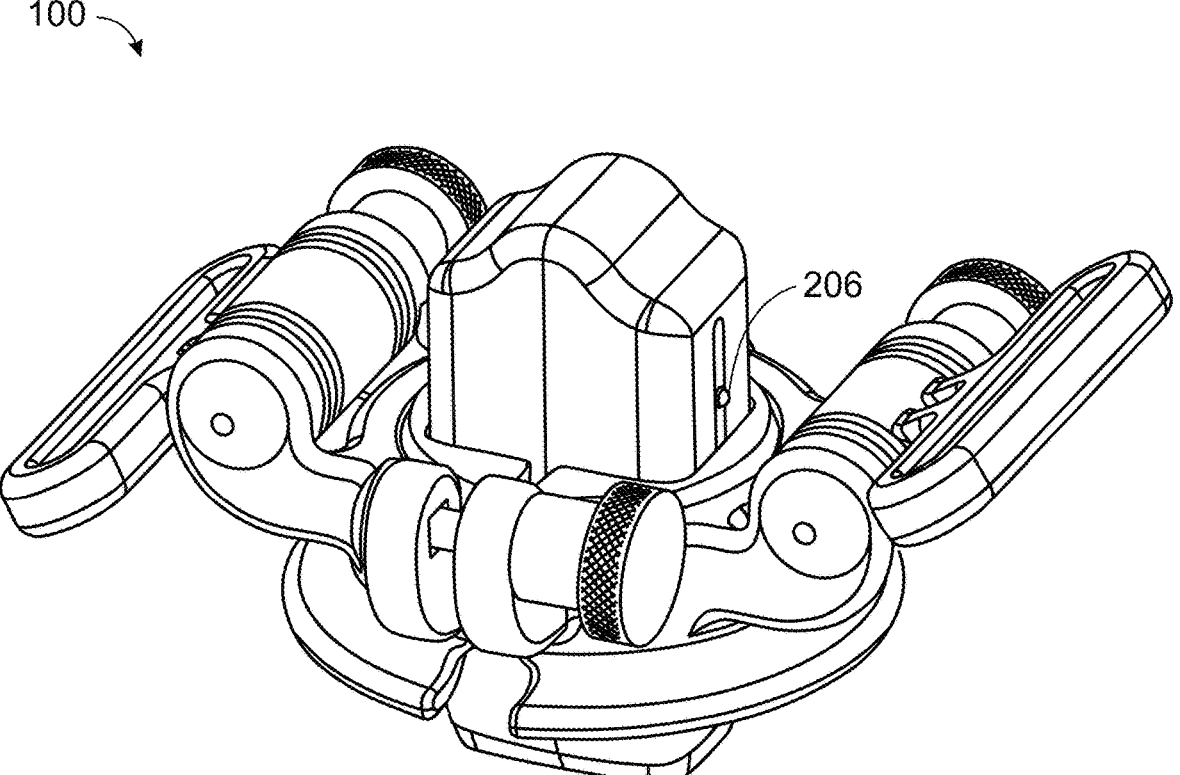
FIG. 25 is a diagram of a mechanism that locks the base off of a surface of the subject.

FIG. 25 is a diagram of a mechanism that locks the base 110 off of a surface of the subject. The wearable device 100 and the ultrasound probe 200 may include features that are configured to temporarily lock the base 110 and/or the cup 500 in a position off of the surface of the subject. For example, as shown in FIG. 25, the ultrasound probe 200 may include balls 206 that interface with detents provided in the mount 130. When engaged with the detents, the balls 206 hold the base 110 and/or the cup 500 off of the surface of the subject while the operator scans with the ultrasound probe 200. This may be useful when the operator is initially scanning around with the ultrasound probe 200 to find an improved, or optimal, acoustic window and the operator does not desire to have the increased friction experienced when the base 110 and/or the cup 500 are in contact with the subject.

Figure 26:
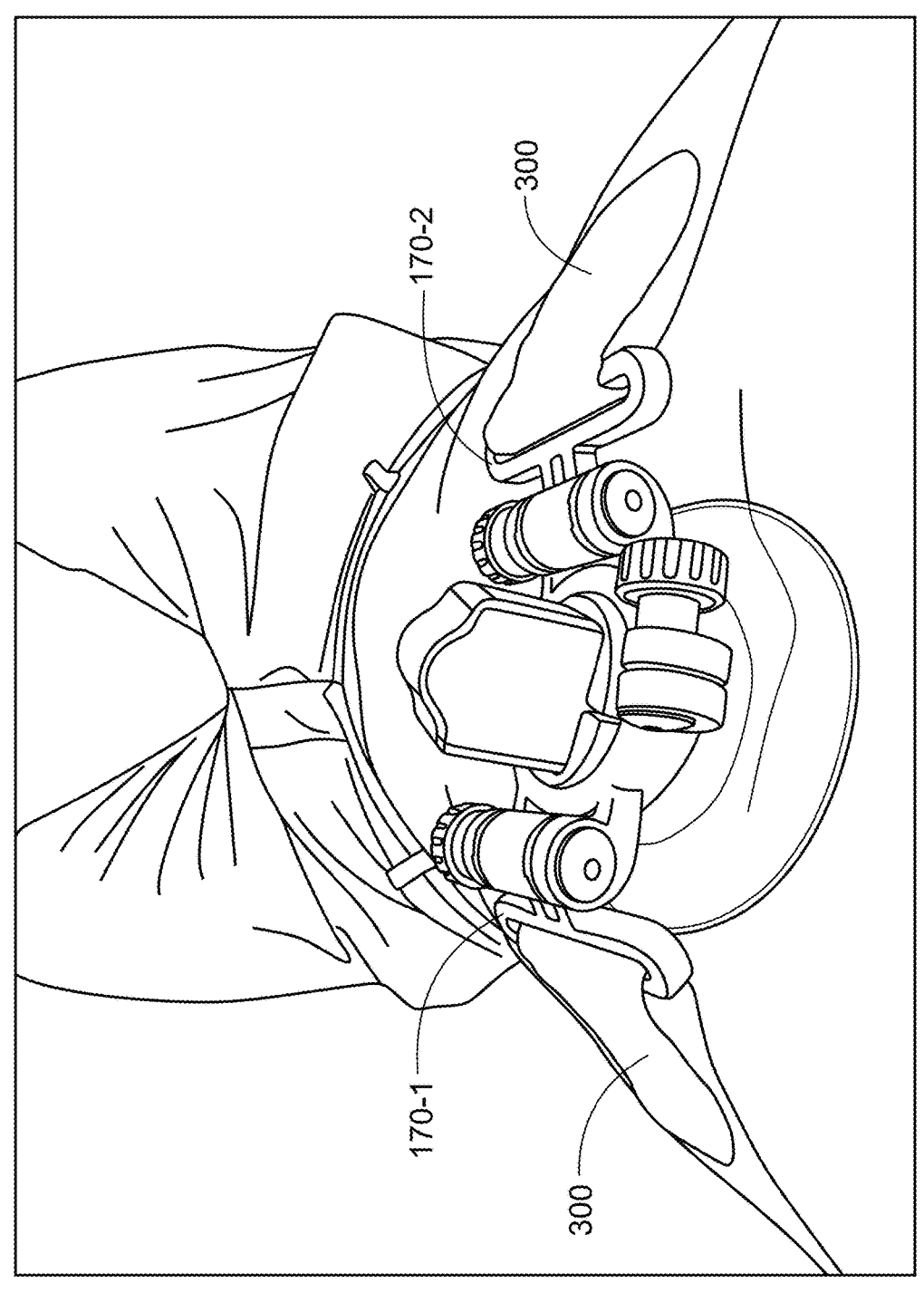
FIG. 26 is a diagram of the strap connectors interfacing with the strap.

FIG. 26 is a diagram of the strap connectors 170 interfacing with the strap 300.

According to an embodiment, the strap connector 170-1 and the strap connector 170-2 may each include a length of the strap 300 in an internal tensioning system. The ultrasound probe 200 may be initially placed in a desired position and orientation while the strap 300 is loose. Then, the internal tensioning system of each strap connector 170 may tighten the strap 300 to the desired tension to secure the ultrasound probe 200 in the desired position and orientation. According to an embodiment, the internal tensioning system may automatically provide a preconfigured tension to secure the ultrasound probe 200. Additionally, or alternatively, the internal tensioning system may include a braking system to inhibit retraction to prevent sudden retraction of the strap 300.

Figure 27:
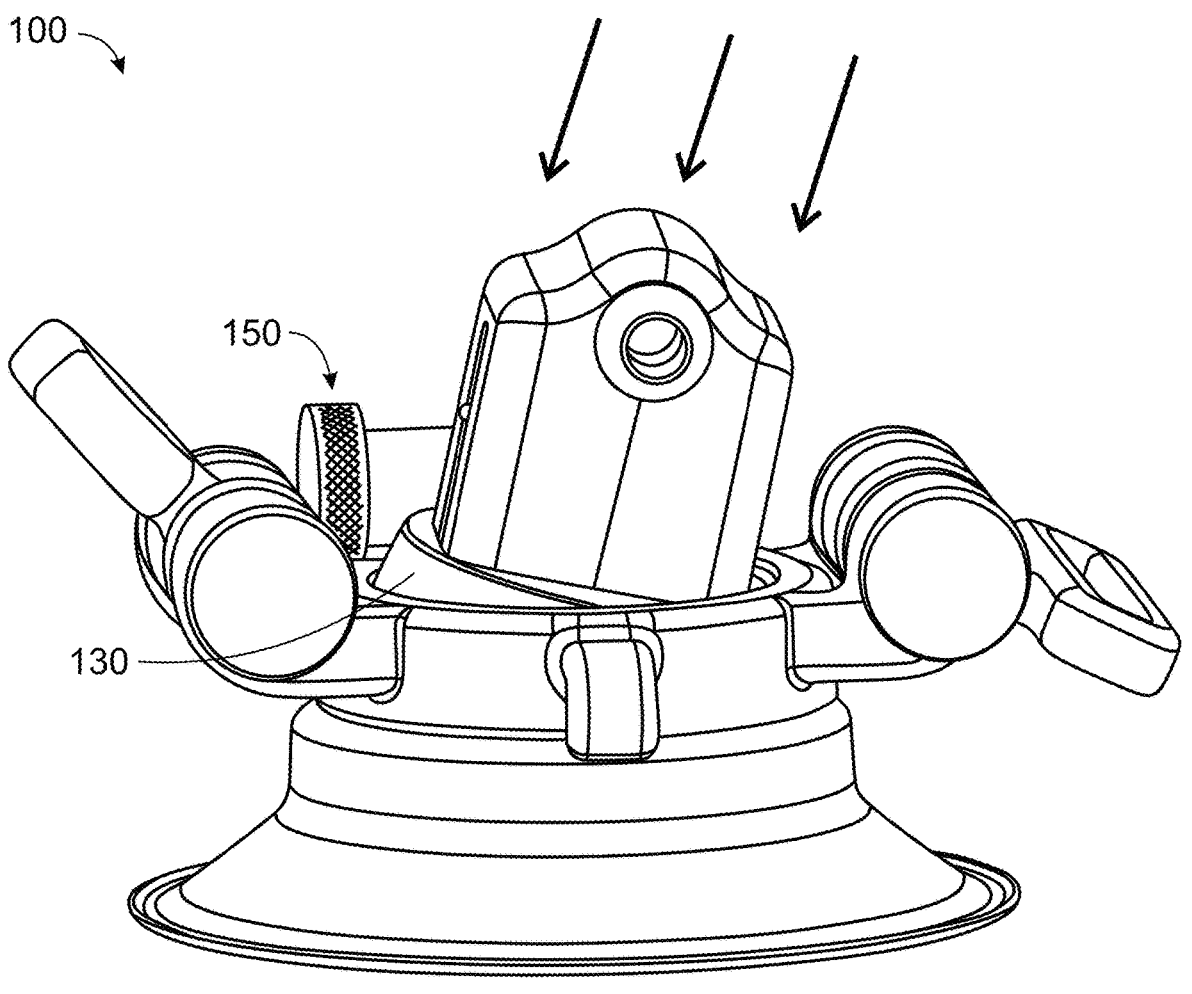
FIG. 27 is a diagram of a wearable device that does not include a channel in the base or the mount.

FIG. 27 is a diagram of the wearable device 100 that does not include a channel in the base 110 or mount 130. According to an embodiment, the lock 150 may be configured to press, or compress, the mount 130 such that the mount 130 is locked in a particular orientation with respect to the base 110. For example, as shown in FIG. 27, the lock 150, when locked, may press the mount 130 in the direction shown by the arrows. By this configuration, the mount 130 may secure the ultrasound probe 200 at a particular orientation with respect to the base 110.

Figure 28:
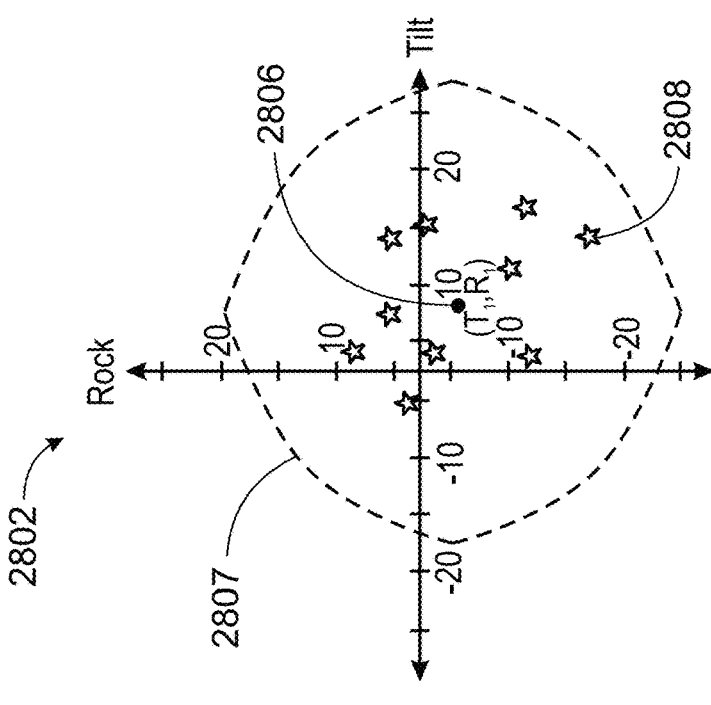
FIG. 28 is a diagram of range of motion profiles for wearable devices.
Figure 28:
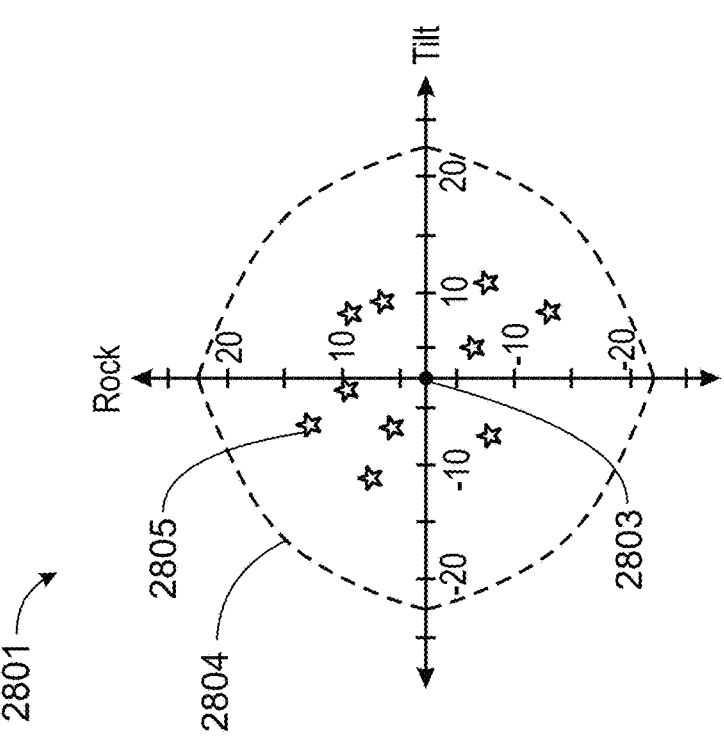

FIG. 28 is a diagram of range of motion profiles 2800 for wearable devices 100. As shown in FIG. 28, a first range of motion profile 2801 may have a center point 2803 having a tilt value of 0 and a rock value of 0. The first range of motion profile 2801 may include a maximum range of motion envelope 2804. A specific point 2805 having a specific tilt value and a specific rock value may correspond to a particular subject. As further shown, a second range of motion profile 2802 may have a center point 2806 having a tilt value of $T_1$ and a rock value of $R_1$. The second range of motion profile 2802 may include a maximum range of motion envelope 2807. A specific point 2808 having a specific tilt value and a specific rock value may correspond to a particular subject.

FIG. 29 is a diagram of the base 110 that does not include strap connectors 170. According to an embodiment, the wearable device 100 may be configured to adhere, or be secured, to the subject without the usage of the strap 300. In this case, the base 110 might not include the strap connector 170-1 or the strap connector 170-2. According to an embodiment, the base 110 may adhere to the subject via an adhesive. Alternatively, the cup 500 may adhere to the subject via friction, suction, or the like. Accordingly, it should be understood that some embodiments herein do not include the strap 300 or require usage of the strap 300.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A wearable device comprising:
   a mount including a spherical outer surface, and an opening configured to receive a probe;
   a base comprising an inner circumferential surface that interfaces with the spherical outer surface of the mount to selectively rotate the mount about at least one axis of the base; and
   a lock that locks a position of the probe relative to the mount and that locks the probe at an orientation relative to the base, wherein:
   the mount includes a first channel,
   the base includes a second channel, and
   the lock closes, or narrows, the first channel and the second channel to lock the position of the probe relative to the mount and lock the probe at the orientation relative to the base.

2. The wearable device of claim 1, further comprising:
   one or more strap connectors that attach a strap to the base and that are lockable at different angular positions.

3. The wearable device of claim 1, wherein the lock locks an amount of protrusion of the probe below a contact surface of the base.

4. The wearable device of claim 1, further comprising:

an adapter that attaches to the probe, and that interfaces with an internal surface of the opening of the spherical mount.

5. The wearable device of claim 1, further comprising:

a cup that attaches to the base and that is configured to contact a surface of a wearer of the wearable device.

6. The wearable device of claim 5, wherein the cup is configured to conform to the surface of the wearer of the wearable device.

7. The wearable device of claim 5, wherein the cup includes a substantially circular profile.

8. The wearable device of claim 5, wherein the cup includes a substantially elliptical profile.

9. The wearable device of claim 1, wherein the probe includes one or more stops that prevent movement of the probe beyond a particular position with respect to the mount.

10. The wearable device of claim 1, wherein the base includes an integrated cable hook that secures a cable of the probe.

11. The wearable device of claim 5, wherein the base includes a first keyed feature that interfaces with a second keyed feature of a cup to lock an orientation of the cup relative to the base.

12. The wearable device of claim 1, further comprising:

one or more strap connectors that are lockable at positions located above a contact surface of the base.

13. The wearable device of claim 1, wherein the probe includes a section having a substantially non-uniform profile, wherein the wearable device further comprises an adapter that includes an inner surface that attaches to the section of the probe, and that includes an outer surface that interfaces with an inner surface of the mount to permit the probe to move relative to the mount.

14. The wearable device of claim 1, wherein:

the base includes rotational fiducial markings, the mount includes a rotational fiducial indicator.

15. The wearable device of claim 1, wherein:

the probe includes a ball, the mount includes a detent, and the ball is configured to engage with the detent to hold the wearable device off of a surface of a wearer of the wearable device.

16. The wearable device of claim 1, further comprising:

one or more straps to secure the wearable device to a wearer of the wearable device; and a set of strap connectors corresponding to the one or more straps to connect the one or more straps to the base.

17. The wearable device of claim 1, further comprising:

the probe, wherein the probe includes a section having a substantially uniform profile to permit the probe to move relative to the mount.

18. The wearable device of claim 1, wherein the probe is an ultrasound probe.

19. A wearable device comprising:

a mount including a spherical outer surface, and an opening configured to receive a probe;

a base comprising an inner circumferential surface that interfaces with the spherical outer surface of the mount to selectively rotate the mount about at least one axis of the base; and a lock that locks a position of the probe relative to the mount and that locks the probe at an orientation relative to the base, wherein the lock is the only lock of the wearable device that locks the position of the probe relative to the mount and that locks the probe at the orientation relative to the base.

20. A wearable device comprising:

a probe;

a mount including a spherical outer surface, and an opening configured to receive the probe;

a base comprising an inner circumferential surface that interfaces with the spherical outer surface of the mount to selectively rotate the mount about at least one axis of the base; and a lock that locks a position of the probe relative to the mount and that locks the probe at an orientation relative to the base, wherein the probe includes one or more stops that prevent movement of the probe beyond a particular position with respect to the mount, or wherein the probe includes a ball, the mount includes a detent, and the ball is configured to engage with the detent to hold the wearable device off of a surface of a wearer of the wearable device.

* * * * *